(12) United States Patent
Che et al.

(10) Patent No.: US 8,530,659 B2
(45) Date of Patent: Sep. 10, 2013

(54) PHARMACEUTICAL COMPOSITION CONTAINING CYCLOMETALATED N-HETEROCYCLIC CARBENE COMPLEXES FOR CANCER TREATMENT

(75) Inventors: Chi Ming Che, Hong Kong (CN); Raymond Wai-Yin Sun, Hong Kong (CN); Lok Fung Chow, Hong Kong (CN); Jing Yan, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 115 days.

(21) Appl. No.: 12/913,395

(22) Filed: Oct. 27, 2010

(65) Prior Publication Data

US 2011/0098264 A1   Apr. 28, 2011

Related U.S. Application Data

(60) Provisional application No. 61/255,667, filed on Oct. 28, 2009, provisional application No. 61/301,752, filed on Feb. 5, 2010.

(51) Int. Cl.
| | | |
|---|---|---|
| *A61K 31/555* | (2006.01) | |
| *C07F 1/12* | (2006.01) | |
| *C07F 15/00* | (2006.01) | |
| *A61P 35/00* | (2006.01) | |

(52) U.S. Cl.
USPC .............................................. 546/4; 514/188

(58) Field of Classification Search
USPC ............................................ 514/188; 546/4
See application file for complete search history.

(56) References Cited

U.S. PATENT DOCUMENTS

2009/0110750 A1* 4/2009 Greener ........................ 424/618
2009/0278453 A1  11/2009 Yam et al.

OTHER PUBLICATIONS

Au et al., J. Am. Chem. Soc., 2009, 131 (25), pp. 9076-9085.*
Fawcett et al., Dalton Trans., 2009, 6861-6870.*
Che. et al. Gold (III) Porphyrins as a new class of anticancer drugs: cytotoxicity, DNA binding and induction of apoptosis in human cervix epitheloid cancer cells. Chem. Commuication, 2003, pp. 1718-1719.
Shaw. Gold-Based Therapeutic Agents. Chem. Review, 1999, vol. 99, pp. 2589-2600.
Kelland. The resurgence of platinum-based cancer chemotherapy. Nature Reviews, vol. 7, Aug. 2007, pp. 573-584.
Au, et al. Luminescent Cyclometalated N-Heterocyclic Carbene-Containing Organogold (III) Complexes: Synthesis, Characterization, Electrochemistry, and Photophysical Studies, Journal of American Chemical Society, 2009, 131, pp. 9076-9085.
Bourissou et al. Stable Carbenes, Chem. Rev. 2000, 100, pp. 39-91.
Chan et al. Luminescent Donor-Acceptor Platinum(II) Complexes. Coordination Chemistry Review, 132, 1994, pp. 87-97.
Arduengo III et al. Synthesis of a Reverse Ylide from a Nucleophilic Carbene. Journal of American Chemical Society, 1991, 113, pp. 9704-9705.
Lowe et al. Cytotoxicity of 2,2':6',2"—Terpyridineplatinum(II) Complexes against Human Ovarian Carcinoma, Journal of Medicinal Chemistry, 1999, 42, pp. 3167-3174.
Herrmann et al. Chiral Oxazoline/Imidazoline-2-ylidene Complexes, Organometallics 1998, 17, pp. 2162-2168.
Grant et al. Binding of Platinum(II) Intercalation Reagents to Deoxyribonucleic Acid. Dependence on Base-Pair Composition, Nature of the Intercalator, and Ionic Strength. Biochemistry, 1979, vol. 18, No. 26, pp. 5762-5769.
Herrmann et al. N-Heterocyclic Carbenes. Angew. Chem. Int. Ed. Engl., 1997, 36, pp. 2162-2187.
Unger et al. Blue phosphorescent emitters: new N-heterocyclic platinum(II) tetracarbene complexes. Chem. Comm., 2008, pp. 3263-3265.
Huang et al. Efficient Cross-Coupling of Aryl Chlorides with Aryl Grignard Reagents (Kumada Reaction) Mediated by a Palladium/Imidazolium Chloride System. Journal of American Chemical Society, 1999, 121, pp. 9889-9890.
Quezada et al. Synthesis and structural characterization of two bis(imidazol-2-ylidene) complexes of Pt(II). Journal of Organometallic Chemistry, 671, (2003), pp. 183-186.
Liu et al. Synthesis, crystal structure and photophysical properties of N-heterocyclic carbene Pd(II), Pt(II) complexes and iodine adduct. Polyhedron 22 (2003), pp. 1515-1521.
Fantasia et al. Electronic Properties of N-Heterocyclic Carbene (NHC) Ligands: Synthetic, Structural, and Spectroscopic Studies of (NHC)Platinum(II) Complexes. Organometallics 2007, 26, pp. 5880-5889.
Liu et al. Formation of the Flourescent Complexes [(carbene)2MII(CN)2] (M=Ni, Pd, Pt) by C-C Bond Cleavage of CH3CN. Organometallics 2004, 23, pp. 610-614.
Fantasia et al. Insertion of a N-Heterocyclic Carbene (NHC) into a Platinum-Olefin Bond. Organometallics 2007, 26, pp. 3286-3288.
Coronnello et al. Mechanisms of Cytotoxicity of Selected Organogold (III) Compounds. Journal of Medicinal Chemistry, 2005, vol. 48, No. 21, pp. 6761-6765.

* cited by examiner

*Primary Examiner* — Sreeni Padmanabhan
*Assistant Examiner* — Jason A Deck
(74) *Attorney, Agent, or Firm* — Turocy & Watson, LLP

(57) ABSTRACT

The present disclosure is related to a pharmaceutical composition for treatment of cancer comprising a cyclometalated N-heterocyclic carbene complex. The cyclometalated N-heterocyclic carbene complex contains a gold(III) or a platinum(II) atom. The pharmaceutical composition possesses anti-cancer activity such as the induction of cell death, inhibition of cellular proliferation, inhibition of topoisomerase and/or poisoning of topoisomerase.

21 Claims, 5 Drawing Sheets

PHARMACEUTICAL COMPOSITION CONTAINING CYCLOMETALATED N-HETEROCYCLIC CARBENE COMPLEXES FOR CANCER TREATMENT

CROSS-REFERENCE TO RELATED APPLICATIONS

This application claims priority to provisional application Ser. No. 61/255,667, filed on Oct. 28, 2009 and to provisional application Ser. No. 61/301,752, filed on Feb. 5, 2010, both of which are incorporated herein by reference.

TECHNICAL FIELD

Described herein are pharmaceutical compositions containing a cyclometalated N-heterocyclic carbene complex, methods of making cyclometalated N-heterocyclic carbene complexes, and methods of using the cyclometalated N-heterocyclic carbene complexes including the treatment of cancer.

BACKGROUND

The success of cisplatin and its derivatives as anticancer agents has stimulated the development of metal-based compounds, including that of platinum and gold, for anticancer treatment [L. Kelland, *Nat. Rev. Cancer* 2007, 7, 573; C. F. Shaw III, *Chem. Rev.* 1999, 99, 2589]. In this context, extensive investigations on the biological properties of platinum(II), gold(I) and gold(III) have been reported. However, the development of the metal-based, particularly gold(III), as potential anti-cancer agents has been hampered by their poor stability in solution [M. Coronnello, E. Mini, B. Caciagli, M. A. Cinellu, A. Bindoli, C. Gabbiani, L. Messori, *J. Med. Chem.* 2005, 48, 6761]. To our knowledge, very few cytotoxic gold(III) compounds such as $[Au(bipy^c\text{-}H)(OH)][PF_6]$ (bipy$^c$-H =deprotonated 6-(1,1-dimethylbenzyl)-2,2'-bipyridine), $[Au(dmamp)Cl_2]$ [dmamp=2-(dimethylaminomethyl)phenyl], and gold(III) tetraarylporphyrins [C.-M. Che, R. W.-Y. Sun, W.-Y. Yu, C.-B. Ko, N. Zhu, H. Sun, *Chem. Commun.* 2003, 1718], have been reported to have significant stability.

The synthesis and photophysical properties of various cyclometalated gold(III) N-heterocyclic complexes have been reported by Yam et al [*J. Am. Chem. Soc.* 2009, 131, 9076; US 2009/0278453 A1]. Yet, the biological properties, notably the anti-cancer properties, of these complexes are completely unknown in the literature.

Cyclometalated platinum(II) complexes containing π-aromatic ligands have long been known to be metallointercalators for double-stranded DNA as the planar metal complex cations can insert between DNA base pairs through ligand-ligand π-π stacking interactions [Chan, C. W.; Cheng, L. K.; Che, C. M. *Coord. Chem. Rev.* 1994, 132, 87]. Extensive studies have revealed that $[Pt^{II}(terpy)(X)]^+$ (terpy=2,2':6',2"-terpyridine, X=chloride, 2-aminoethanethiolate, ethyl 2-mercaptoacetate, 2-hydroxyethanethiolate or cysteine), $[Pt^{II}(N^{\frown}N)(en)]^{2+}$ (N$^{\frown}$N=1,10-phenanthroline or 2,2'-bipyridine; en=ethylenediamine) and $[Pt^{II}(CNN)(X)]^+$ (CNN=6-phenyl-2,2'-bipyridine, X=pyridine, 4-aminopyridine or N,N'-bis(isonicotinyl)-1,6-hexane-diamine) can intercalate DNA and display cytotoxic activities [(a) Howe-Grant, M.; Lippard, S. J. *Biochemistry* 1979, 18, 5762; (b) Lowe, G.; Droz, A. S.; Vilaivan, T.; Weaver, G. W.; Park, J. J.; Pratt, J. M.; Tweedale, L.; Kelland, L. R. *J. Med. Chem.* 1999, 42, 3167]. Platinum(II) complexes have other potential biological applications because they are usually kinetically stable, soluble in water and do not form insoluble hydrated oxides under physicological conditions. The tendency of square-planar platinum(II) complexes to form one-dimensional columnar stacks in their crystal structures and the aromaticity and size of chelating aromatic ligand such as terpy, N$^{\frown}$N or CNN all contribute to the ability of platinum(II) complexes to bind to DNA by intercalation.

The chemistry of N-heterocyclic carbene (NHC) has long been confined to metal coordination complexes derived from azolium compounds, which was started by Öfele and Wanzlick in 1968. In 1991, Arduengo successfully synthesized stable free NHCs, which had subsequently been used as ligands for transition metal complexes [Arduengo, A. J. III; Kline, M.; Calabrese, J. C.; Davidson, F. *J. Am. Chem. Soc.* 1991, 113, 9704.]. Since then, many transition metal carbene complexes have been reported [Herrmann, W. A.; Köcher, C. *Angew. Chem. Int. Ed. Engl.* 1998, 36, 2162. (b) Bourissou, D.; Olivier, G.; Francois, P. G; Bertrand, G. *Chem. Rev.* 2000, 100, 39]. A leading motive is the advantage of NHC as ligand in the development of organometallic catalysts, whereas NHC ligands extend the scope of applications reached by phosphanes (functionalized, chiral, water-soluble, and immobilized derivatives). Metal-NHC complexes are usually stable to heat, air, and moisture [Herrmann, W. A.; Goossen, L. J.; Spigler, M. *Organometallics.* 1998, 17, 2162], and the coordination of carbene ligand to metal ion can be performed under simple and mild conditions. This feature stimulates a surge of interest, and many transition metal complexes containing NHC ligands derived from imidazolium ions have been synthesized [Herrmann, W. A.; Köcher, C. *Angew. Chem. Int. Ed. Engl.* 1997, 96, 2162]. Metal-N-heterocyclic carbene complexes have been used as catalysts for a spectrum of catalytic reactions, including Heck, Suzuki, and Kumada coupling reactions, alkene metathesis, and hydrosilylation [Huang, J.; Nolan, S. P. *J. Am. Chem. Soc.* 1999, 121, 9889]. In general, NHC ligands are accessible and their strong σ-donating character resemble to that of phosphine ligands [Herrmann, W. A.; Köcher, C. *Angew. Chem. Int. Ed. Engl.* 1997, 96, 2162]. In literature, however, there are few $Pt^{II}$—NHC complexes [(a) Unger, Y.; Zeller, A.; Ahrens, S.; Strassner, T. *Chem. Commun.* 2008, 3263. (b) Liu, Q. X.; Xu, F. B.; Li, Q. S.; Song, H. B.; Zhang, Z. Z. *Organometallics* 2004, 23, 610. (c) Fantasia, S.; Jacobsen, H.; Cavallo, L.; Nolan, S. P. *Organometallics,* 2007, 26, 3286. (d) Fantasia, S.; Jacobsen, H.; Cavallo, L.; Nolan, S. P. *Organometallics,* 2007, 26, 5880. (e) Liu, Q. X.; Song, H. B.; Xu, F. B.; Li, Q. S.; Zeng, X. S.; Leng, X. B.; Zhang, Z. Z. *Polyhedron* 2003, 22, 1515. (f) Quezada, C. A.; Garrison, J. C.; Tessier, C. A.; Youngs, W. J. *J. Organomet. Chem.,* 2003, 671, 183.], and none of reported examples contain chelating cyclometalated ligand such as 6-phenyl-2,2'-bipyridine.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

Described herein is directed to a pharmaceutical composition for treatment of cancer comprising a cyclometalated N-heterocyclic carbene complex.

In one embodiment, a method for cancer treatment resulting in induction of cell death, inhibition of cellular proliferation, or inhibition of topoisomerase comprises administering in need thereof a composition comprising an effective amount of a cyclometalated carbene complex. The cyclometalated carbene complex is a gold(III) or platinum(II) complex described herein can be represented by one or more structural formulae of I, II, III or IV:

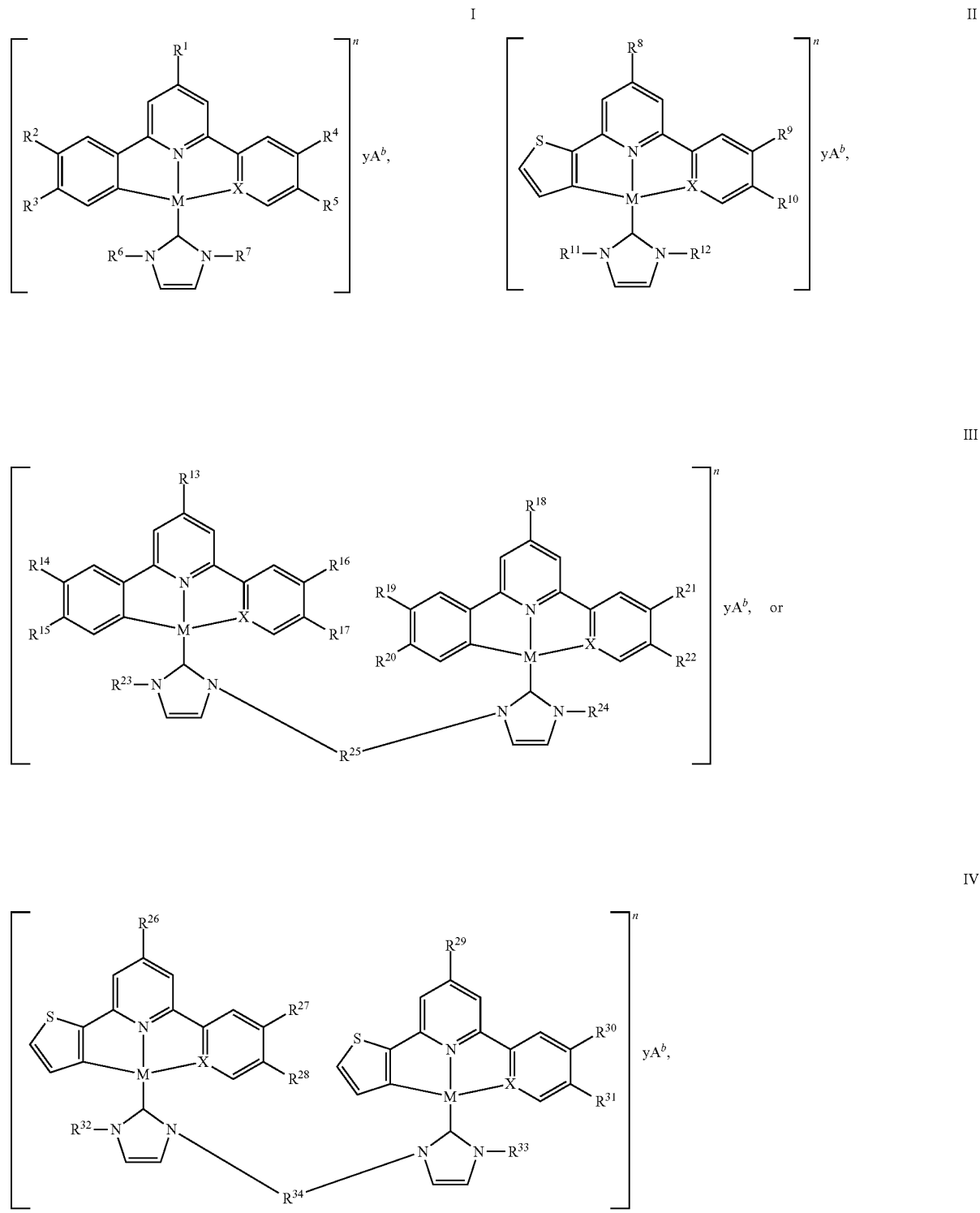

or a pharmaceutically acceptable salt thereof, wherein,

M is selected from the metal ion of $Au^{3+}$ or $Pt^{2+}$;

X is selected from a carbon atom or a nitrogen atom;

$R^1$, $R^8$, $R^{13}$, $R^{18}$, $R^{26}$, and $R^{29}$ are each independently selected from the group consisting of —H,

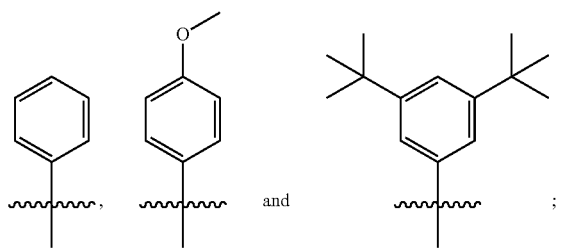

$R^2$, $R^3$, $R^4$, $R^5$, $R^9$, $R^{10}$, $R^{14}$, $R^{15}$, $R^{16}$, $R^{17}$, $R^{19}$, $R^{20}$, $R^{21}$, $R^{22}$, $R^{27}$, $R^{28}$, $R^{31}$, and $R^{32}$ are each independently selected from the group consisting of —H and —$NO_2$; or each pair of $R^2$ and $R^3$; $R^4$ and $R^5$; $R^9$ and $R^{10}$; $R^{14}$ and $R^{15}$; $R^{16}$ and $R^{17}$; $R^{19}$ and $R^{20}$; $R^{21}$ and $R^{22}$; $R^{27}$ and $R^{28}$; $R^{31}$ and $R^{32}$ is independently joined together to form

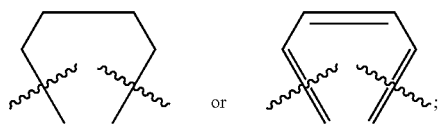

$R^6$, $R^7$, $R^{11}$, $R^{12}$, $R^{23}$, $R^{24}$, $R^{32}$ and $R^{33}$ are each independently selected from the group consisting of —$CH_3$, —$C_2H_5$, —$C_3H_7$, —$C_4H_9$, —$CH_2OH$, —$C_2H_4OH$, —$C_3H_6OH$, —$C_4H_8OH$,

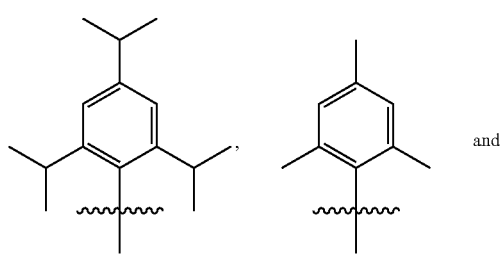

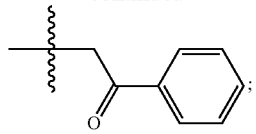

$R^{25}$ and $R^{34}$ are each independently selected from the group consisting of —$CH_2$—, —$C_2H_4$—, —$C_3H_6$— and —$C_4H_8$—;

Each A is independently a pharmaceutically acceptable counter-ion;

n is an integer ranging from 0 to +4;

b is an integer ranging from −4 to −1;

y is equal to the absolute value of n/b when n is >0; and $yA^b$ is absence when n is equal to 0.

These gold(III) and platinum(II) complexes are stable in air and physiological conditions and display higher anti-cancer activity than the clinically used cisplatin. In addition, the ease of syntheses and structural modification also helps these complexes for prevalent clinical applications.

DETAILED DESCRIPTION

Figure 1:
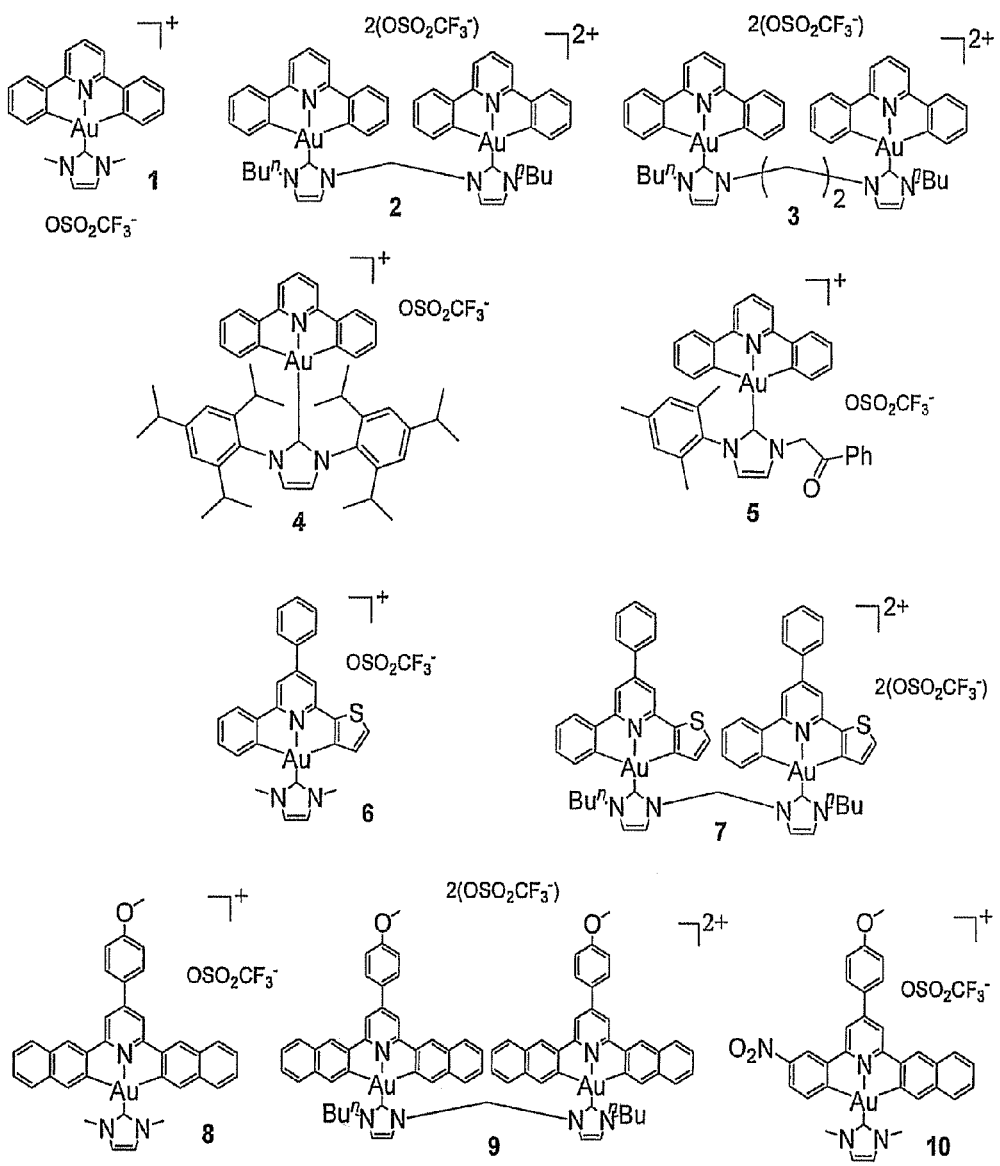
FIG. 1 shows chemical structures of the gold-based cyclometalated N-heterocyclic carbene complexes (complexes 1-10) in accordance with the present invention.

Disclosed are pharmaceutical compositions for treatment of cancer comprising a Group 10 or 11 transition metal cyclometalated N-heterocyclic carbene complex, such as a gold (III) [or Au(III) or $Au^{III}$ or $Au^{3+}$]cyclometalated N-heterocyclic carbene complex or a platinum(II) [or Pt(II) or $Pt^{II}$ or $Pt^{2+}$] cyclometalated N-heterocyclic carbene complex. A pharmaceutical composition can contains at least one cyclometalated N-heterocyclic carbene complex in amount effective for an anti-cancer activity such as the induction of cell death, inhibition of cellular proliferation, inhibition of topoisomerase and/or poisoning of topoisomerase.

As noted herein, "cyclometalated N-heterocyclic carbene complex" refers to a molecule of a platinum(II) or a gold(III) ion connected to a tridentate ligand and a N-heterocyclic carbene ligand, which can be represented by structural formulae I, II, III or IV, or a pharmaceutically acceptable salt thereof:

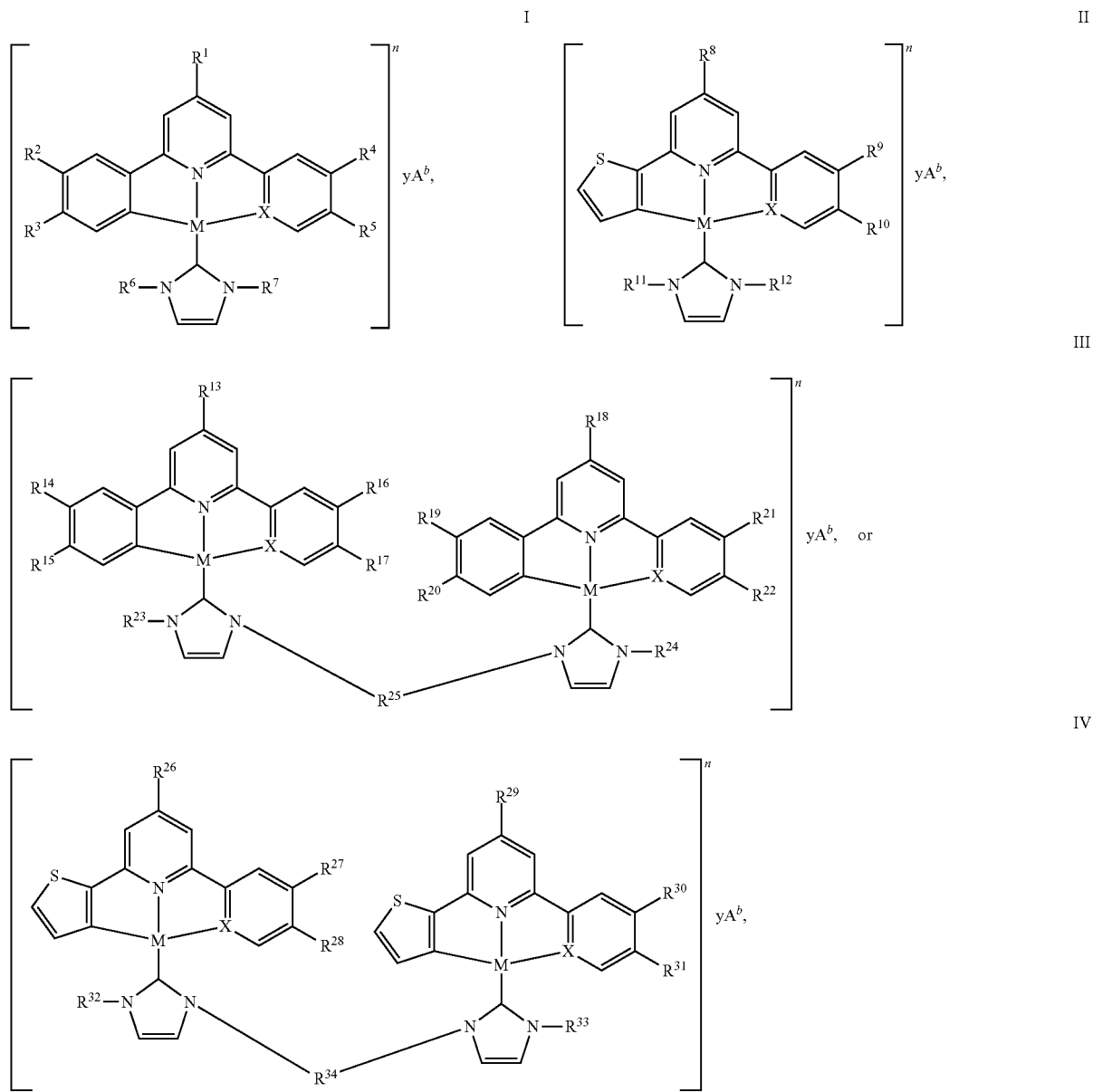

or a pharmaceutically acceptable salt thereof, wherein,
M is selected from the metal ion of $Au^{3+}$ or $Pt^{2+}$;
X is selected from a carbon atom or a nitrogen atom;
$R^1$, $R^8$, $R^{13}$, $R^{18}$, $R^{26}$, and $R^{29}$ are each independently selected from the group consisting of —H,

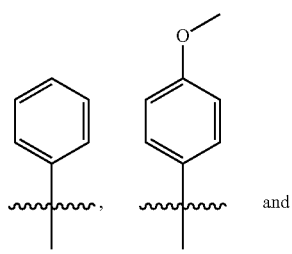

$R^2$, $R^3$, $R^4$, $R^5$, $R^9$, $R^{10}$, $R^{14}$, $R^{15}$, $R^{16}$, $R^{17}$, $R^{19}$, $R^{20}$, $R^{21}$, $R^{22}$, $R^{27}$, $R^{28}$, $R^{31}$, and $R^{32}$ are each independently selected from the group consisting of —H and —$NO_2$; or each pair of $R^2$ and $R^3$; $R^4$ and $R^5$; $R^9$ and $R^{10}$; $R^{14}$ and $R^{15}$; $R^{16}$ and $R^{17}$; $R^{19}$ and $R^{20}$; $R^{21}$ and $R^{22}$; $R^{27}$ and $R^{28}$; $R^{31}$ and $R^{32}$ is independently joined together to form

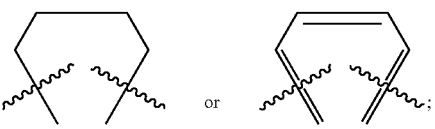 [SMILES: *CCCC* ; *=C/C=C\C=*]

$R^6$, $R^7$, $R^{11}$, $R^{12}$, $R^{23}$, $R^{24}$, $R^{32}$ and $R^{33}$ are each independently selected from the group consisting of —$CH_3$, —$C_2H_5$, —$C_3H_7$, —$C_4H_9$, —$CH_2OH$, —$C_2H_4OH$, —$C_3H_6OH$, —$C_4H_8OH$,

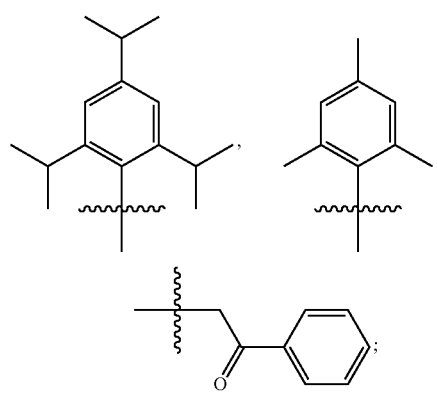

and

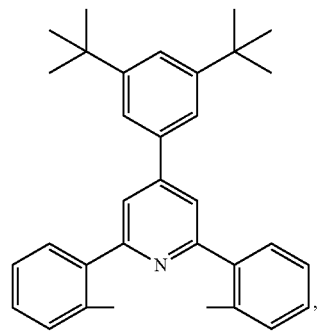

$R^{25}$ and $R^{34}$ are each independently selected from the group consisting of —CH$_2$—, —C$_2$H$_4$—, —C$_3$H$_6$— and —C$_4$H$_8$—;

Each A is independently a pharmaceutically acceptable counter-ion;

n is an integer ranging from 0 to +4;

b is an integer ranging from −4 to −1;

y is equal to the absolute value of n/b when n is >0; and yA$^b$ is absence when n is equal to 0.

As used herein, the term "tridentate ligand" refers to a di-anionic substituted/non-substituted 2,6-diphenylpyridine (hereinafter CNC) ligand or a mono-anionic substituted/non-substituted 6-phenyl-2,2'-bipyridine (hereinafter CNN) ligand. Non-limiting examples of the CNC ligands are:

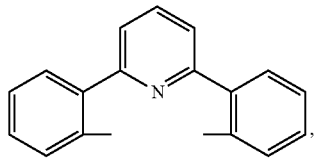

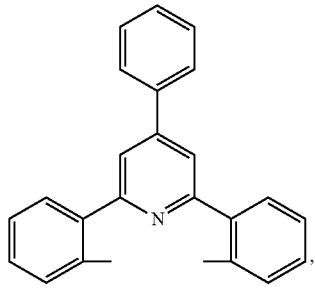

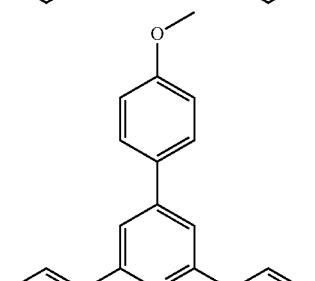

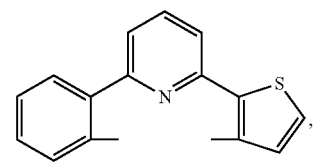

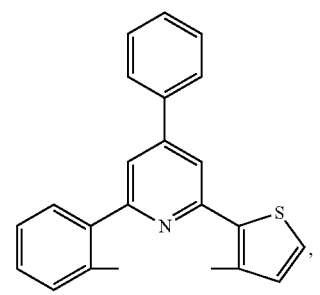

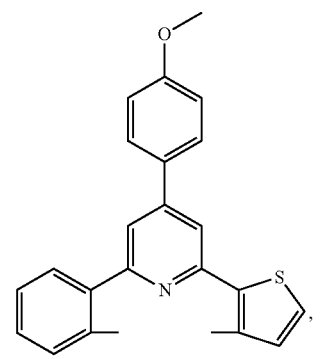

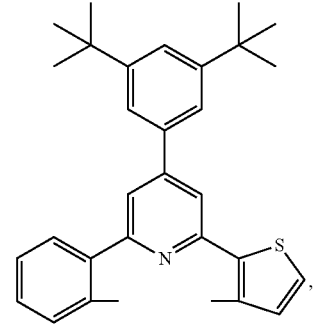

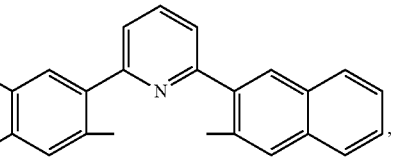

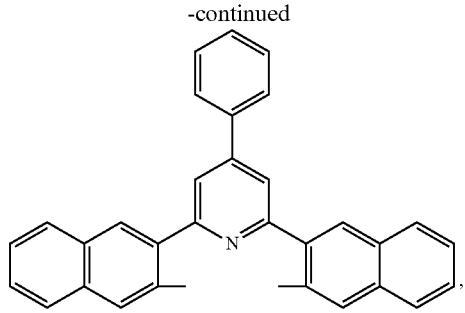
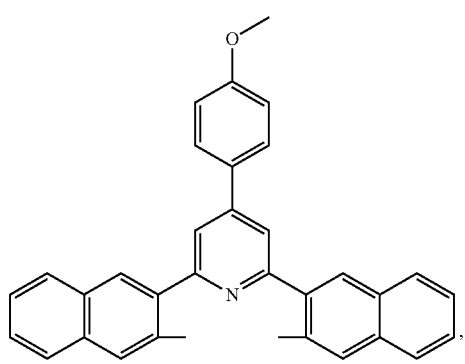
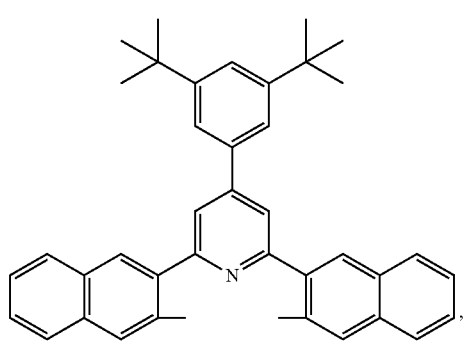
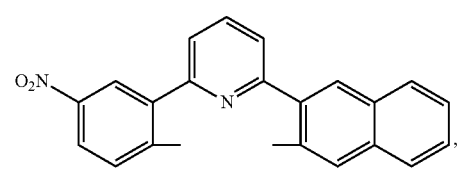
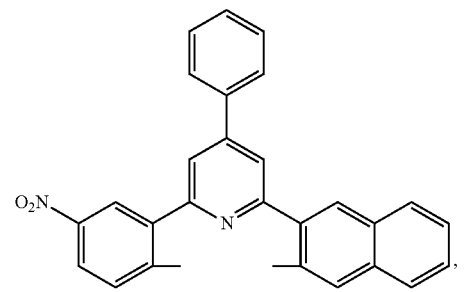
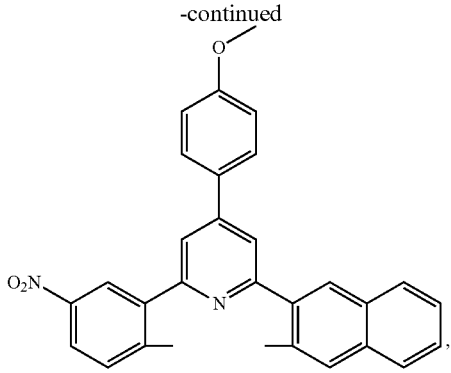
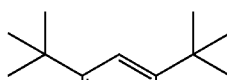, and
non-limiting examples of the CNN ligands are:
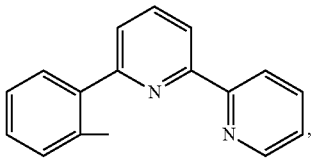
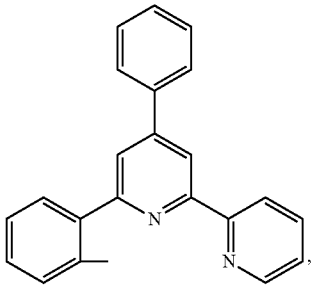
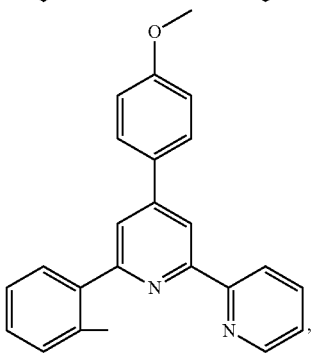

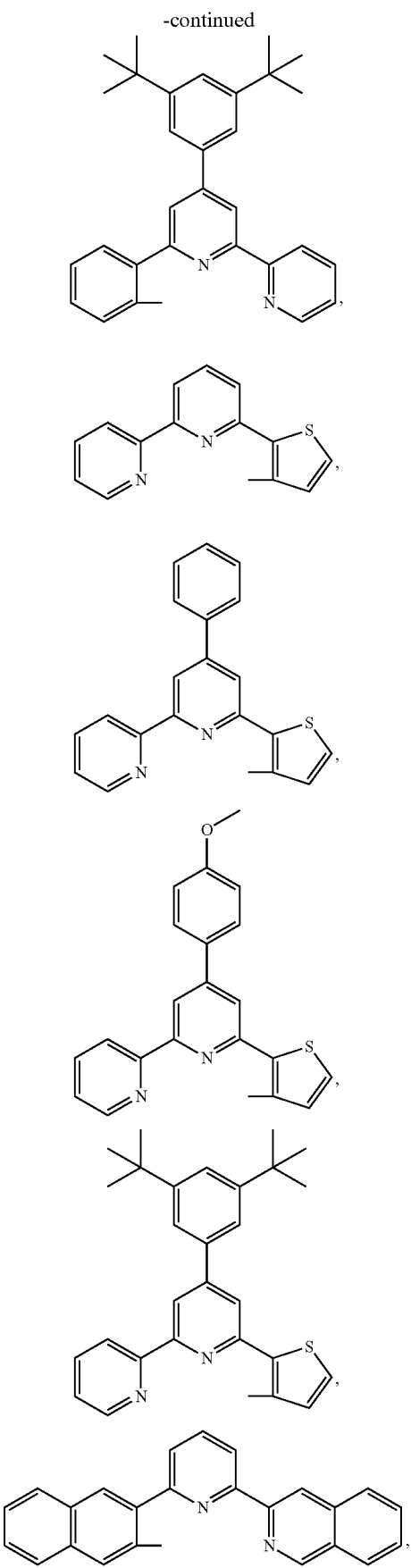

-continued

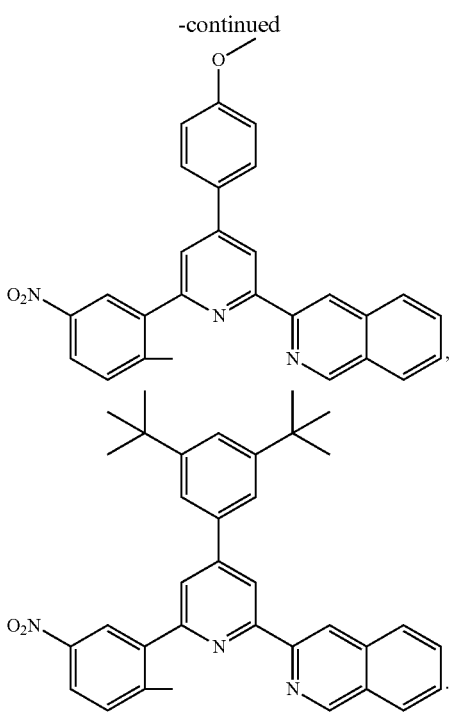

As used herein, the term "N-heterocyclic carbene" refers to a ligand having one of the following chemical structures:

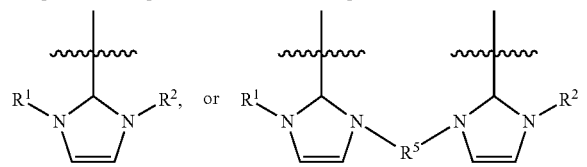

wherein:

R$^1$ and R$^2$ are each independently selected from the group consisting of alkyl having 1 to 5 carbon atoms such as —CH$_3$, —C$_2$H$_5$, —C$_3$H$_7$, —C$_4$H$_9$, alkanol having 1 to 5 carbon atoms such as —CH$_2$OH, —C$_2$H$_4$OH, —C$_3$H$_6$OH, —C$_4$H$_8$OH, substituted benzyl such as

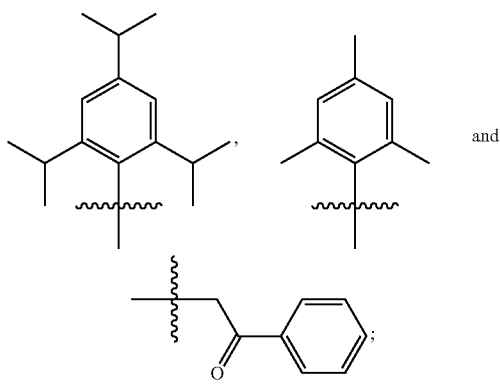

R$^5$ is selected from the group consisting of alkyl having 1 to 5 carbon atoms such as —CH$_2$—, —C$_2$H$_4$—, —C$_3$H$_6$— and —C$_4$H$_8$—. In one embodiment, the N-heterocyclic carbene is coordinated with the gold(III) or platinum(II) ion.

It will be understood that the di-anionic CNC ligand or the mono-anionic CNN ligand can form a non-neutral complex with the gold(III) or the platinum(II) ion. For instance, the net positive charge on the gold(III) or the platinum(II) ion can be greater than the absolute net negative charge of the CNC or the CNN ligand. In view of this, there can be at least one counter-anion coordinated to the cyclometalated N-heterocyclic carbene complex for charge neutralization. Accordingly, the phrase "pharmaceutically acceptable salt," as used herein, includes salts formed from charged cyclometalated N-heterocyclic carbene complex and counter-anion(s).

In one embodiment of the cyclometalated N-heterocyclic carbene complex, n is an integer selected from 1, 2, 3 and 4.

As used herein, the phrase "counter-anion" refers to an ion associated with a positively charged cyclometalated N-heterocyclic carbene complex. Non-limiting examples of counter-ions include halogens such as fluoride, chloride, bromide, iodide; sulfate; phosphate; trifluoromethanesulfonate; acetate; nitrate; perchlorate; acetylacetonate; hexafluorophosphate and hexafluoroacetylacetonate.

In one embodiment, the structure of the cyclometalated N-heterocyclic carbene complex can be either in monomeric (formulae I and II) or dimeric (formulae III and IV) form. Also, the cyclometalated N-heterocyclic carbene complex can exist as a single molecule or aggregated molecules (an agglomerate).

As used herein, the phrase of "pharmaceutically acceptable carrier" means a carrier or combination of carrier ingredients approved by a regulatory agency of the Federal or a state government or listed in the U.S. Pharmacopoeia or other generally recognized pharmacopoeia for use in animals, mammals, and more particularly in humans. Non-limiting examples of pharmaceutically acceptable carriers include liquids, such as water and oils, including those of petroleum, animal, vegetable, or synthetic origin. Water is a frequently used when the compound of the invention is administered intravenously. Saline solutions and aqueous dextrose and glycerol solutions can also be employed as liquid vehicles, particularly for injectable solutions.

As noted above, the present invention relates to a pharmaceutical composition for cancer treatment.

In one embodiment, the invention relates to a pharmaceutical for cancer treatment by induction of cell death (including but not limited to apoptosis) of cancer cells comprising administering with a responsive form of cancer a composition comprising an effective amount of one or more cyclometalated N-heterocyclic carbene complexes.

In another embodiment, the invention relates to a pharmaceutical for cancer treatment by inhibition of the proliferation of cancer cells comprising administering with a responsive form of cancer a composition comprising an effective amount of one or more cyclometalated N-heterocyclic carbene complexes.

In another embodiment, the invention relates to a pharmaceutical for cancer treatment by inhibition of topoisomerase or poisoning of topoisomerase comprising administering with a responsive form of cancer a composition comprising an effective amount of one or more cyclometalated N-heterocyclic carbene complexes.

The cyclometalated N-heterocyclic carbene complexes of this invention can be represented by one or more of structural formulae I, II, III or IV, or a pharmaceutically acceptable salt thereof:

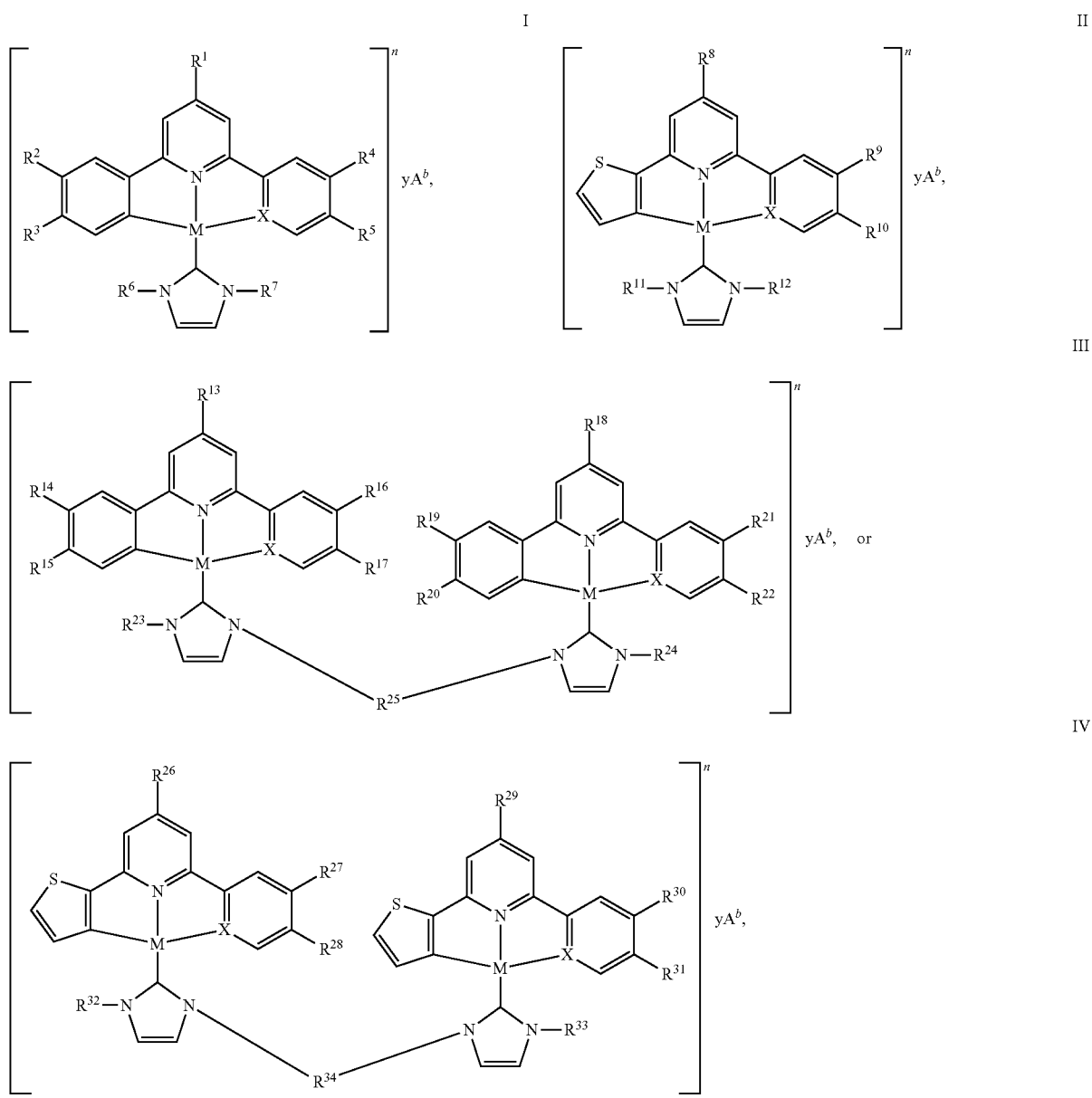

or a pharmaceutically acceptable salt thereof, wherein,
M is selected from the metal ion of $Au^{3+}$ or $Pt^{2+}$;
X is selected from a carbon atom or a nitrogen atom;
$R^1$, $R^8$, $R^{13}$, $R^{18}$, $R^{26}$, and $R^{29}$ are each independently selected from the group consisting of —H,

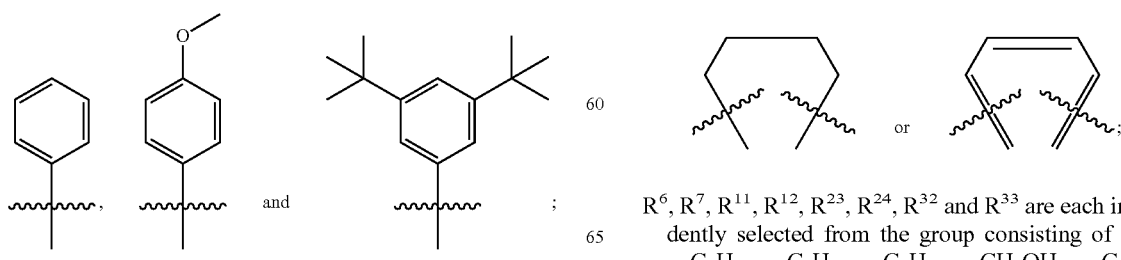

$R^2$, $R^3$, $R^4$, $R^5$, $R^9$, $R^{10}$, $R^{14}$, $R^{15}$, $R^{16}$, $R^{17}$, $R^{19}$, $R^{20}$, $R^{21}$, $R^{22}$, $R^{27}$, $R^{28}$, $R^{31}$, and $R^{32}$ are each independently selected from the group consisting of —H and —$NO_2$; or each pair of $R^2$ and $R^3$; $R^4$ and $R^5$; $R^9$ and $R^{10}$; $R^{14}$ and $R^{15}$; $R^{16}$ and $R^{17}$; $R^{19}$ and $R^{20}$; $R^{21}$ and $R^{22}$; $R^{27}$ and $R^{28}$; $R^{31}$ and $R^{32}$ is independently joined together to form $R^6$, $R^7$, $R^{11}$, $R^{12}$, $R^{23}$, $R^{24}$, $R^{32}$ and $R^{33}$ are each independently selected from the group consisting of —$CH_3$, —$C_2H_5$, —$C_3H_7$, —$C_4H_9$, —$CH_2OH$, —$C_2H_4OH$, —$C_3H_6OH$, —$C_4H_8OH$,

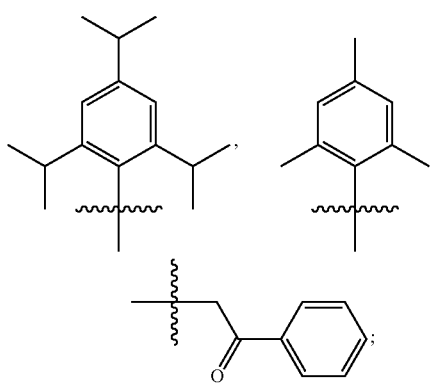

R²⁵ and R³⁴ are each independently selected from the group consisting of —CH₂—, —C₂H₄—, —C₃H₆— and —C₄H₈—;

Each A is independently a pharmaceutically acceptable counter-ion;

n is an integer ranging from 0 to +4;

b is an integer ranging from −4 to −1;

y is equal to the absolute value of n/b when n is >0; and yA$^b$ is absence when n is equal to 0.

In one embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein, M is Au³⁺;
X is a carbon atom;
R¹, R², R³, R⁴, and R⁵ are each —H;
R⁶ and R⁷ are each —CH₃;
A is a OSO₂CF₃ anion;
n is +1;
b is −1; and
y is 1 (complex 1).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula III or a pharmaceutically acceptable salt thereof, wherein, M is Au³⁺;
X is a carbon atom;
R¹³ and R¹⁸ are each —H;
R¹⁴, R¹⁵, R¹⁶, R¹⁷, R¹⁹, R²⁰, R²¹ and R²² are each —H;
R²³ and R²⁴ are each —C₄H₉;
R²⁵ is —CH₂—;
A is a OSO₂CF₃ anion;
n is +2;
b is −1; and
y is 2 (complex 2).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula III or a pharmaceutically acceptable salt thereof, wherein, M is Au³⁺;
X is a carbon atom;
R¹³ and R¹⁸ are each —H;
R¹⁴, R¹⁵, R¹⁶, R¹⁷, R¹⁹, R²⁰, R²¹ and R²² are each —H;
R²³ and R²⁴ are each —C₄H₉;
R²⁵ is —C₂H₄—;
A is a OSO₂CF₃ anion;
n is +2;
b is −1; and
y is 2 (complex 3).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein, M is Au³⁺;
X is a carbon atom;
R¹, R², R³, R⁴, and R⁵ are each —H;
R⁶ and R⁷ are each

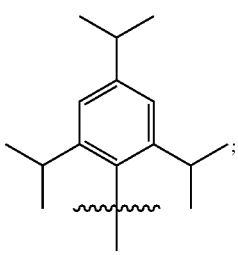 [SMILES: *c1c(C(C)C)cc(C(C)C)cc1C(C)C]

A is a OSO₂CF₃ anion;
n is +1;
b is −1; and
y is 1 (complex 4).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein, M is Au³⁺;
X is a carbon atom;
R¹, R², R³, R⁴, and R⁵ are each —H;
R⁶ is

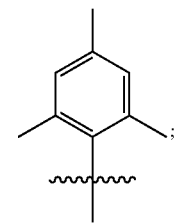

$R^7$ is

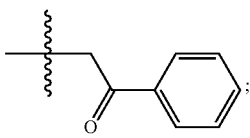 [SMILES: *CC(=O)c1ccccc1]

A is a $OSO_2CF_3$ anion;
n is +1;
b is −1; and
y is 1 (complex 5).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula II or a pharmaceutically acceptable salt thereof, wherein,
M is $Au^{3+}$;
X is a carbon atom;
$R^8$ is

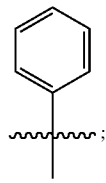 [SMILES: *c1ccccc1]

$R^9$ and $R^{10}$ are each —H;
$R^{11}$ and $R^{12}$ are each —$CH_3$;
A is a $OSO_2CF_3$ anion;
n is +1;
b is −1; and
y is 1 (complex 6).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula IV or a pharmaceutically acceptable salt thereof, wherein,
M is $Au^{3+}$;
X is a carbon atom;
$R^{26}$ and $R^{29}$ are each

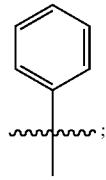 [SMILES: *c1ccccc1]

$R^{27}$, $R^{28}$, $R^{30}$ and $R^{31}$ are each —H;
$R^{32}$ and $R^{33}$ are each —$C_4H_9$;
$R^{34}$ is —$CH_2$—;
A is a $OSO_2CF_3$ anion;
n is +2;
b is −1; and
y is 2 (complex 7)

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein,
M is $Au^{3+}$;
X is a carbon atom;
$R^1$ is

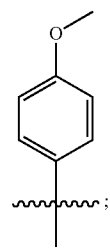

each pair of $R^2$ and $R^3$, and $R^4$ and $R^5$ is joined together to form

$R^6$ and $R^7$ are each —$CH_3$;
A is a $OSO_2CF_3$ anion;
n is +1;
b is −1; and
y is 1 (complex 8).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula III or a pharmaceutically acceptable salt thereof, wherein,
M is $Au^{3+}$;
X is a carbon atom;
$R^{13}$ and $R^{18}$ are each

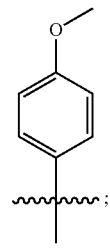

each pair of $R^{14}$ and $R^{15}$; $R^{16}$ and $R^{17}$; $R^{19}$ and $R^{20}$; $R^{21}$ and $R^{22}$, is joined together to form

$R^{23}$ and $R^{24}$ are each —$C_4H_9$;
$R^{25}$ is —$CH_2$—;
A is a $OSO_2CF_3$ anion;
n is +2;
b is −1; and
y is 2 (complex 9).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula II or a pharmaceutically acceptable salt thereof, wherein,
M is $Au^{3+}$;
X is a carbon atom;
$R^8$ is

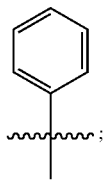 [SMILES: *c1ccccc1]

$R^9$ is —$NO_2$;
$R^{10}$ is —H;
$R^{11}$ and $R^{12}$ are each —$CH_3$;
A is a $OSO_2CF_3$ anion;
n is +1;
b is −1; and
y is 1 (complex 10).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein,
M is $Pt^{2+}$;
X is a nitrogen atom;
$R^1$, $R^2$, $R^3$, $R^4$, and $R^5$ are each —H;
$R^6$ and $R^7$ are each —$CH_3$;
A is a $PF^6$ anion;
n is +1;
b is −1; and
y is 1 (complex 11).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein,
M is $Pt^{2+}$;
X is a nitrogen atom;
$R^1$, $R^2$, $R^3$, $R^4$, and $R^5$ are each —H;
$R^6$ and $R^7$ are each —$C_2H_5$;
A is a $PF^6$ anion;
n is +1;
b is −1; and
y is 1 (complex 12).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein,
M is $Pt^{2+}$;
X is a nitrogen atom;
$R^1$, $R^2$, $R^3$, $R^4$, and $R^5$ are each —H;
$R^6$ and $R^7$ are each —$C_3H_7$;
A is a $PF^6$ anion;
n is +1;
b is −1; and
y is 1 (complex 13).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein,
M is $Pt^{2+}$;
X is a nitrogen atom;
$R^1$, $R^2$, $R^3$, $R^4$, and $R^5$ are each —H;
$R^6$ and $R^7$ are each —$C_4H_9$;
A is a $PF^6$ anion;
n is +1;
b is −1; and
y is 1 (complex 14).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula III or a pharmaceutically acceptable salt thereof, wherein,
M is $Pt^{2+}$;
X is a nitrogen atom;
$R^{13}$, $R^{14}$, $R^{15}$, $R^{16}$, $R^{17}$, $R^{18}$, $R^{19}$, $R^{20}$, $R^{21}$ and $R^{22}$ are each —H;
$R^{23}$ and $R^{24}$ are each —$C_4H_9$;
$R^{25}$ is —$CH_2$
A is a $PF^6$ anion;
n is +2;
b is −1; and
y is 2 (complex 15).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula III or a pharmaceutically acceptable salt thereof, wherein,
M is $Pt^{2+}$;
X is a nitrogen atom;
$R^{13}$, $R^{14}$, $R^{15}$, $R^{16}$, $R^{17}$, $R^{18}$, $R^{19}$, $R^{20}$, $R^{21}$ and $R^{22}$ are each —H;
$R^{23}$ and $R^{24}$ are each —$C_4H_9$;
$R^{25}$ is —$C_3H_6$
A is a $PF^6$ anion;
n is +2;
b is −1; and
y is 2 (complex 16).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein, M is $Pt^{2+}$;
X is a nitrogen atom;
$R^1$ is

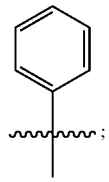 [SMILES: *c1ccccc1]

$R^2$, $R^3$, $R^4$, and $R^5$ are each —H;
$R^6$ and $R^7$ are each —$C_3H_7$;
A is a $PF^6$ anion;
n is +1;
b is −1; and
y is 1 (complex 17).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein, M is $Pt^{2+}$;
X is a nitrogen atom;
$R^1$ is

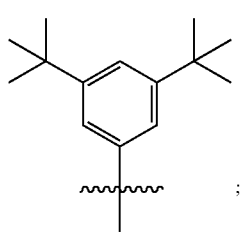 [SMILES: *c1cc(C(C)(C)C)cc(C(C)(C)C)c1]

$R^2$, $R^3$, $R^4$, and $R^5$ are each —H;
$R^6$ and $R^7$ are each —$C_3H_7$;
A is a $PF^6$ anion;
n is +1;
b is −1; and
y is 1 (complex 18).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula III or a pharmaceutically acceptable salt thereof, wherein, M is $Pt^{2+}$;
X is a nitrogen atom;
$R^{13}$ and $R^{18}$ are each

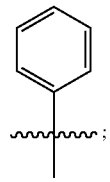

$R^{14}$, $R^{15}$, $R^{16}$, $R^{17}$, $R^{19}$, $R^{20}$, $R^{21}$ and $R^{22}$ are each —H;
$R^{23}$ and $R^{24}$ are each —$C_4H_9$;
$R^{25}$ is —$CH_2$
A is a $PF^6$ anion;
n is +2;
b is −1; and
y is 2 (complex 19).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula III or a pharmaceutically acceptable salt thereof, wherein, M is $Pt^{2+}$;
X is a nitrogen atom;
$R^{13}$ and $R^{18}$ are each

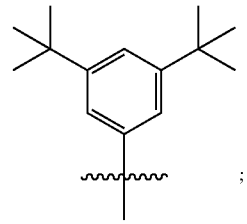 [SMILES: *c1cc(C(C)(C)C)cc(C(C)(C)C)c1]

$R^{14}$, $R^{15}$, $R^{16}$, $R^{17}$, $R^{19}$, $R^{20}$, $R^{21}$ and $R^{22}$ are each —H;
$R^{23}$ and $R^{24}$ are each —$C_4H_9$;
$R^{25}$ is —$CH_2$
A is a $PF^6$ anion;
n is +2;
b is −1; and
y is 2 (complex 20).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein, M is $Pt^{2+}$;
X is a nitrogen atom;
$R^1$ is —H;
each pair of $R^2$ and $R^3$, and $R^4$ and $R^5$ is joined together to form

$R^6$ and $R^7$ are each —$C_3H_7$;
A is a $PF_6$ anion;
n is +1;

b is −1; and
y is 1 (complex 21).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula III or a pharmaceutically acceptable salt thereof, wherein, M is $Pt^{2+}$;
X is a nitrogen atom;
$R^{13}$ and $R^{18}$ are each —H;
each pair of $R^{14}$ and $R^{15}$, $R^{16}$ and $R^{17}$, $R^{19}$ and $R^{20}$, and $R^{21}$ and $R^{22}$ is joined together to form

$R^{23}$ and $R^{24}$ are each —$C_4H_9$;
$R^{25}$ is —$CH_2$
A is a $PF^6$ anion;
n is +2;
b is −1; and
y is 2 (complex 22).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein, M is $Pt^{2+}$;
X is a nitrogen atom;
$R^1$, $R^2$, $R^3$, $R^4$, and $R^5$ are each —H;
$R^6$ is

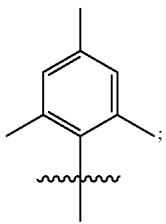

$R^7$ is —$C_3H_6OH$;
A is a $PF^6$ anion;
n is +1;
b is −1; and
y is 1 (complex 23).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein, M is $Pt^{2+}$;
X is a nitrogen atom;
$R^1$, $R^2$ and $R^3$ are each —H;
$R^4$ and $R^5$ are joined together to form

$R^6$ and $R^7$ are each $C_3H_7$;
A is a $PF^6$ anion;
n is +1;
b is −1; and
y is 1 (complex 24).

In another embodiment, the invention relates to a pharmaceutical composition for treatment of cancer by induction of cell death, inhibition of cellular proliferation, inhibition of topoisomerase and/or poisoning of topoisomerase comprising an effective amount of a cyclometalated N-heterocyclic carbene complex of formula I or a pharmaceutically acceptable salt thereof, wherein, M is $Pt^{2+}$;
X is a nitrogen atom;
$R^1$, $R^2$ and $R^3$ are each —H;
$R^4$ and $R^5$ are joined together to form

$R^6$ is $C_4H_9$;
$R^7$ is —$C_2H_4OH$;
A is a $PF^6$ anion;
n is +1;
b is −1; and
y is 1 (complex 25).

Methods of making the cyclometalated N-heterocyclic carbene complexes as described above generally involve reacting a cyclometalated complex with an N-heterocyclic carbene compound to form the cyclometalated N-heterocyclic carbene complex. In one embodiment, the cyclometalated N-heterocyclic carbene complexes are prepared by deprotonating a N-heterocyclic carbene compound and then reacting the deprotonated N-heterocyclic carbene compound with suitable cyclometalated complex comprising gold or platinum.

After the reaction, the cyclometalated N-heterocyclic carbene complexes are worked up and, if appropriate, purified by processes known to those skilled in the art. Typically, the workup and purification are effected by evaporation, filtration, extraction, column chromatography and/or recrystallization by processes known to those skilled in the art.

EXAMPLES

Example 1

Figure 2:
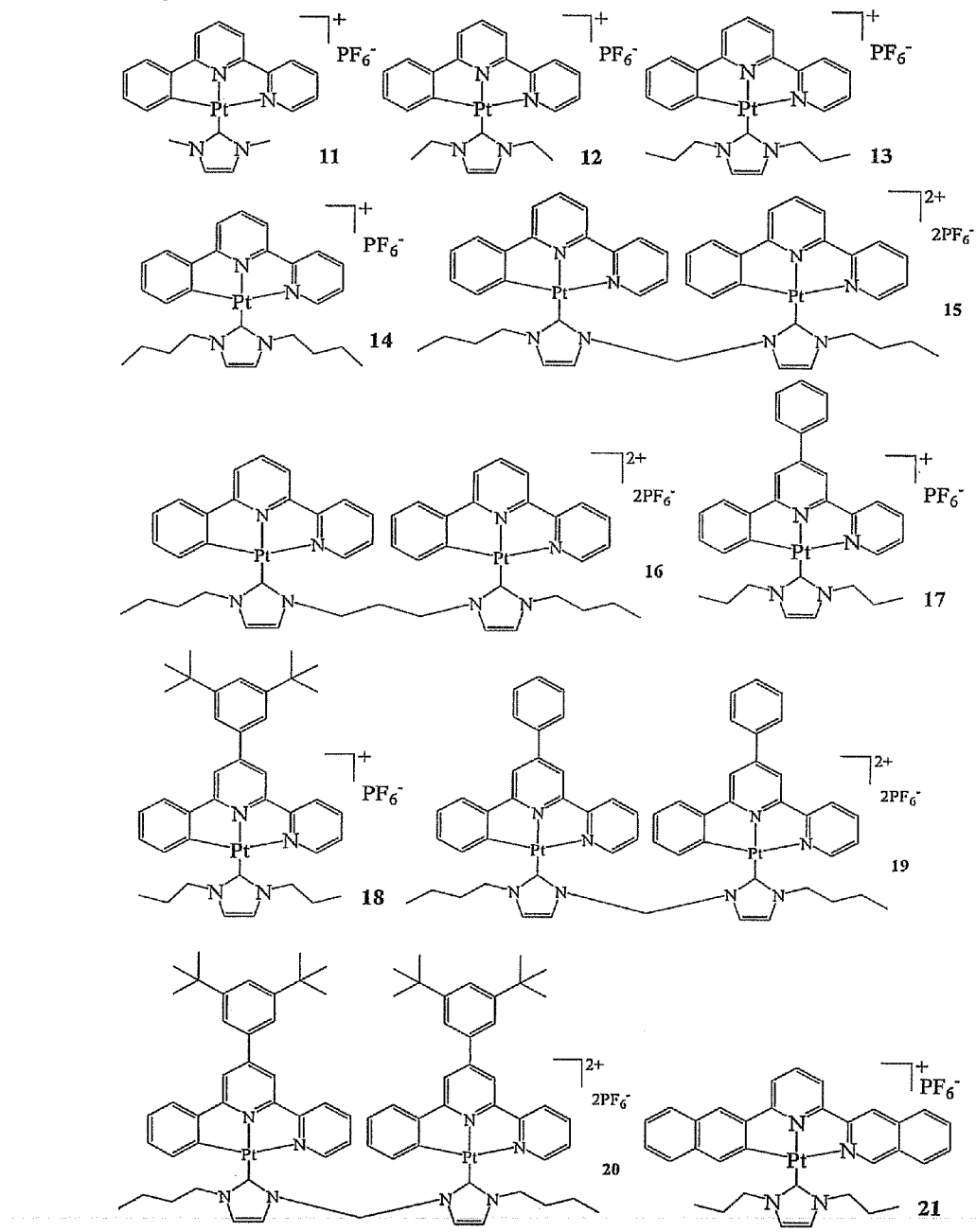
FIG. 2 shows chemical structures of the platinum-based cyclometalated N-heterocyclic carbene complexes (complexes 11-25) in accordance with the present invention.

Preparation and Characterization of the Cyclometalated N-Heterocyclic Carbene Complexes Example 1 illustrates the synthesis and characterization of the gold(III)-based (FIG. 1) and the platinum(II)-based (FIG. 2) cyclometalated N-heterocyclic carbene complexes.

Complex 1 Au(CNC)Cl (40.00 mg, 0.087 mmol), N,N'-dimethylimidazolium iodide (20.61 mg, 0.092 mmol) and KO$^t$Bu (11.20 mg, 0.100 mmol) were refluxed in 25 mL $CH_3CN$ overnight under an inert atmosphere. After 24 hours, a saturated $LiOSO_2CF_3$ solution in $CH_3CN$ was added and the mixture was stirred at room temperature for another 30 minutes. The mixture was gravity filtered and the filtrate was collected. The filtrate was concentrated to about 5 mL, excess Et$_2$O was added and the mixture was kept <10° C. for 1 day. Pale yellow solid was formed.

Yield: 49.32 mg, 82.6%. Anal. Calcd for C$_{23}$H$_{19}$N$_3$O$_3$F$_3$SAu: C, 41.13; H, 2.83; N, 6.26. Found: C, 41.06; H, 3.01; N, 6.56. $^1$H NMR (400 MHz, (CD$_3$)$_2$SO): δ 3.84 (s, 6H, —CH$_3$), 6.94 (d, 2H, J=7.09 Hz), 7.31 (t, 2H, J=6.70), 7.37 (t, 2H, J=7.18), 7.83 (s, 2H), 7.99 (d, 2H, J=7.51 Hz), 8.06 (d, 2H, J=8.03), 8.25 (t, 1H, J=8.01). $^{19}$F NMR (400 MHz, (CD$_3$)$_2$SO): δ −79.32. FAB-MS (+ve, m/z): 522 [M$^+$].

Complex 2: Au(CNC)Cl (100 mg, 0.217 mmol), 1,1'-methylene bis(3-n-butylimidazolium) diiodide (56.20 mg, 0.109 mmol) and KO$^t$Bu (25.80 mg, 0.230 mmol) were refluxed in 20 mL CH$_3$CN under an inert atmosphere overnight.

A yellow colored solution was formed. The solution was treated in a similar manner to that of complex 1, yellow precipitates were crystallized out. Yield: 0.1081 g, 72.5%. Anal. Calcd for C$_{51}$H$_{46}$N$_6$O$_6$F$_6$S$_2$Au$_2$: C, 43.41; H, 3.29; N, 5.96. Found: C, 43.62; H, 3.33; N, 6.08. $^1$H NMR (400 MHz, CD$_3$CN): δ 0.62 (t, 6H, J=7.36, -"Bu), 1.03 (q, 4H, J=7.53, -"Bu), 1.62-1.66 (m, 4H, -"Bu), 4.03 (t, 4H, J=7.11, -"Bu), 6.73 (d, 4H, J=7.34), 6.83 (s, 2H), 6.91 (t, 4H, J=7.39), 7.14 (t, 4H, J=7.60), 7.41 (d, 4H, J=7.73), 7.47 (d, 4H, J=8.04), 7.69 (s, 2H), 8.02 (t, 2H, J=8.02 Hz), 8.09 (s, 2H). $^{19}$F NMR (400 MHz, (CD$_3$CN): δ −79.33. FAB-MS (+ve, m/z): 1261 [M+OSO$_2$CF$_3$]$^+$.

Complex 3: Au(CNC)Cl (100 mg, 0.217 mmol), 1,2-propylene bis(3-n-butylimidazolium) diiodide (57.73 mg, 0.109 mmol) and KO$^t$Bu (25.80 mg, 0.230 mmol) were refluxed in 20 mL CH$_3$CN under an inert atmosphere overnight. A yellow colored solution was formed. The solution was treated in a similar manner to that of complex 1, yellow precipitates were crystallized out. Yield: 0.1163 g, 78%. Anal. Calcd for C$_{53}$H$_{50}$N$_6$O$_6$F$_6$S$_2$Au$_2$: C, 44.23; H, 3.50; N, 5.84. Found: C, 43.96; H, 3.49; N, 5.90. $^1$H NMR (400 MHz, CD$_3$CN): δ 0.69 (t, 6H, J=5.64, -"Bu), 1.13 (q, 4H, -"Bu), 1.66-1.67 (m, 4H, -"Bu), 2.43 (t, 2H, J=6.28), 4.04 (t, 4H, J=5.00), 4.19 (s, 4H), 6.83 (s, 4H), 7.14 (s, 4H), 7.23 (d, 4H, J=5.90), 7.47 (s, 4H), 7.69 (s, 4H), 7.74 (s, 4H), 8.14-8.15 (m, 2H). $^{19}$F NMR (400 MHz, (CD$_3$CN): δ −79.311. ESI-Q-TOF-MS (+ve, m/z): 570 [M]$^{2+}$.

Complex 4: Synthesis similar to that of complex 1, by using Au(CNC)Cl (22.7 mg, 0.049 mmol), carbene (24.9 mg, 0.049 mmol) and KO$^t$Bu (5.7 mg, 0.051 mmol). A pure brown solid was formed. Yield: 28.1 mg, 54.7%. Anal. Calcd for C$_{51}$H$_{60}$N$_3$O$_3$F$_3$SAu: C, 58.39; H, 5.76; N, 4.01. Found: C, 60.18; H, 5.93; N, 4.29. $^1$H NMR (400 MHz, CDCl$_3$): δ 1.56 (s, 36H, —CH$_3$), 2.06-2.19 (m, 6H, —CH—), 6.30 (s, 2H), 6.81 (s, 2H), 7.38-7.44 (m, 2H), 7.46-7.52 (m, 2H), 7.71-7.76 (m, 2H), 7.86-7.91 (m, 2H), 7.97 (t, 2H, J=7.74), 8.26 (s, 2H). $^{19}$F NMR (400 MHz, (CDCl$_3$): δ −72.33. FAB-MS (+ve, m/z): 917 [M$^+$].

Complex 5 Au(CNC)Cl (40.00 mg, 0.087 mmol), substituted imidazolium iodide (20.61 mg, 0.092 mmol) and KO$^t$Bu (11.20 mg, 0.100 mmol) were refluxed in 25 mL CH$_3$CN overnight under an inert atmosphere. After 24 hours, a saturated LiOSO$_2$CF$_3$ solution in CH$_3$CN was added and the mixture was stirred at room temperature for another 30 minutes. The mixture was gravity filtered and the filtrate was collected. The filtrate was concentrated to about 5 mL, excess Et$_2$O was added and the mixture was kept <10° C. for 1 day. Pale yellow solid was formed. Yield: 49.32 mg, 82.6%.

Complex 6: Synthesized and treated similar to that of complex 1. Yield: 93.1 mg, 69.4%. Anal. Calcd for C$_{27}$H$_{22}$N$_3$O$_3$F$_3$S$_2$Au: C, 58.39; H, 5.76; N, 4.01. Found: C, 61.38; H, 6.27; N, 4.18. $^1$H NMR (400 MHz, CD$_3$CN): δ 3.85 (s, 6H, —CH$_3$), 7.02-7.07 (m, 2H), 7.11-7.23 (m, 7H), 7.31 (d, 4H, J=6.17), 8.37 (s, 2H). $^{19}$F NMR (400 MHz, (CDCl$_3$): δ −79.33. FAB-MS (+ve, m/z): 606 [M$^+$].

Complex 7: Synthesized and treated similar to that of complex 2. An orange-brown solid was formed. Anal. Calcd for C$_{59}$H$_{52}$N$_6$O$_6$F$_6$S$_4$Au$_2$: C, 44.93; H, 3.32; N, 5.33. Found: C, 45.36; H, 3.59; N, 5.65. $^1$H NMR (300 MHz, CD$_2$Cl$_2$): δ 0.89-0.97 (m, 6H, -"Bu), 1.31-1.47 (m, 4H -"Bu), 1.79-1.89 (m, 4H, -"Bu), 4.13-4.21 (m, 4H, -"Bu), 6.64-6.68 (m, 2H), 7.14-7.20 (m, 8H), 7.28-7.63 (m, 10H), 7.95-8.06 (m, 8H), 8.61 (s, 2H), 10.28 (s, 2H). FAB-MS (+ve, m/z): 1429 [M$^+$+OSO$_2$CF$_3$], 1279 [M$^+$].

Complex 8: Synthesized and treated similar to that of complex 1, using methoxyphenyl-substituted extended Au(CNC)Cl (104.5 mg, 0.1566 mmol), N,N'-dimethylimidazolium iodide (36.9 mg, 0.1644 mmol) and KO$^t$Bu (20 mg, 0.1700 mmol). Yellow solid was formed. Yield: 106.8 mg, 77.6%. Anal. Calcd for C$_{38}$H$_{30}$N$_3$O$_4$F$_3$SAu: C, 51.94; H, 3.44; N, 4.78. Found: C, 53.27; H, 3.63; N, 4.89. $^1$H NMR (300 MHz, CD$_3$CN): δ 3.81 (s, 3H, —OCH$_3$), 3.85 (s, 6H, —CH$_3$ on carbene), 7.09-7.18 (m, 3H), 7.27-7.29 (m, 1H), 7/50-7.58 (m, 3H), 7.67-7.72 (m, 21-1), 7.84-7.96 (m, 3H), 7.99-8.06 (m, 3H), 8.20 (t, 2H, J=9.92), 8.49 (dd, 1H, J=8.61), 8.54 (d, 1H, J=7.73), 8.80 (s, 1H). $^{19}$F NMR (400 MHz, (CDCl$_3$): 5-79.31. FAB-MS (+ve, m/z): 728 [M$^+$].

Complex 9: Synthesized and treated similar to that of complex 2, using methoxyphenyl-substituted extended Au(CNC)Cl (123.0 mg, 0.1843 mmol), 1,1'-methylene bis(3-n-butylimidazolium) diiodide (47.6 mg, 0.0922 mmol) and KO$^t$Bu (22.4 mg, 0.2000 mmol). An intense yellow solid was formed. Yield: 147.2 mg, 43.7%. Anal. Calcd for C$_{81}$H$_{68}$N$_6$O$_8$F$_6$S$_2$Au$_2$: C, 53.29; H, 3.75; N, 4.60. Found: C, 55.08; H, 3.92; N, 4.72. $^1$H NMR (300 MHz, CD$_3$CN): δ 0.47-0.52 (m, 6H, -"Bu), 0.85-0.96 (m, 4H, -"Bu), 1.79-1.85 (m, 4H, -"Bu), 3.87 (s, 6H, —OCH$_3$), 3.90-3.96 (m, 4H, -"Bu), 6.66-6.69 (m, 2H), 6.76-6.78 (m, 1H), 7.05-7.15 (m, 6H), 7.26-7.37 (m, 3H), 7.48-7.60 (m, 7H), 7.75-7.88 (m, 6H), 7.95-7.98 (m, 4H), 8.05-8.11 (m, 4H), 8.24 (s, 2H), 8.39-8.42 (1H), 8.52 (dd, 2H, J=8.66), 8.84 (s, 2H). $^{19}$F NMR (400 MHz, (CDCl$_3$): δ −79.33. FAB-MS (+ve, m/z): 1674 [M$^+$+OSO$_2$CF$_3$], 1524 [M$^+$].

Complex 10: Synthesized and treated similar to that of complex 1, using methoxyphenyl-substituted extended Au(CNC)Cl (129.7 mg, 0.1958 mmol), N,N'-dimethylimidazolium iodide (48.0 mg, 0.2056 mmol) and KO$^t$Bu (26.0 mg, 0.2300 mmol). A pure brown solid was formed. Yield: 125.8 mg, 73.5%. Anal. Calcd for C$_{34}$H$_{27}$N$_4$O$_6$F$_3$SAu: C, 46.74; H, 3.12; N, 6.41. Found: C, 48.07; H, 3.48; N, 6.58. $^1$H NMR (400 MHz, CD$_3$CN): δ 3.84 (s, 6H, —CH$_3$ on carbene), 3.87 (s, 3H, —OCH$_3$), 7.08-7.16 (m, 3H), 7.56-7.60 (m, 2H), 7.79 (t, 1H, J=8.02), 7.94-7.98 (m, 2H), 8.06 (d, 2H, J=7.90), 8.16 (s, 1H), 8.28 (d, 1H, J=6.47), 8.31 (d, 1H, J=8.18), 8.46 (d, 1H, J=8.67), 8.79 (s, 1H), 9.12 (s, 1H). $^{19}$F NMR (400 MHz, (CDCl$_3$): δ −79.33. FAB-MS (+ve, m/z): 725 [M$^+$].

In general, the platinum(II)-based cyclometalated N-heterocyclic carbene complexes (FIG. 2) can be synthesized by reaction of imidazolium salt of N,N'-dialkylimidazolium halide (alkyl and halide=-CH$_3$ and I$^-$, (ligand 1); —CH$_2$CH$_3$ and I$^-$, (ligand 2); —CH$_2$CH$_2$CH$_3$ and Br$^-$, (ligand 3); —CH$_2$CH$_2$CH$_2$CH$_3$ and Br$^-$ (ligand 4)) or 1,1'-alkylene bis(3-n-butylimidazolium) diiodide [0.5 equivalent; alkyl=methylene, (ligand 5); propylene, (ligand 6)] with equimolar amount of potassium tert-butoxide and appropriate type of precursor [Pt(CNN)Cl] complexes under an inert atmosphere gave corresponding mononuclear and binuclear platinum(II) complexes Analytical data for the [Pt$^{II}_n$(CNN)$_n$(NHC)]$^{n+}$ complexes are shown below:

Complex 11. Yield: 70.1 mg, 84.0%. Anal. Calcd for C$_{21}$H$_{19}$N$_4$PF$_6$Pt: C, 37.78; H, 2.85; N, 8.40. Found: C, 38.01; H, 2.95; N, 8.29. $^1$H NMR (400 MHz, CD$_3$CN): δ 3.82 (s, 6H, —CH$_3$), 6.47 (d, 1H, J=7.40), 7.05 (t, 1H, J=9.86), 7.11 (t, 1H, J=9.15), 7.31 (m, 2H), 7.60 (m, 2H), 7.88 (d, 1H, J=8.14), 8.00 (d, 1H, J=8.01), 8.11 (t, 1H, J=8.05), 8.23 (m, 3H). $^{13}$C NMR (126 MHz, CD$_3$CN): δ 39.03 (Me), 120.54, 123.82, 125.29, 125.92, 126.59, 129.59, 132.51, 137.72, 141.68, 142.57, 153.44 (carbene). $^{31}$P NMR (400 MHz, CD$_3$CN): δ −144.52. $^{19}$F NMR (400 MHz, CD$_3$CN): δ −73.12. FAB-MS (+ve, m/z): 522 [M$^+$].

Complex 12. Yield: 40.1 mg, 85.1%. Anal. Calcd for C$_{23}$H$_{23}$N$_4$PF$_6$Pt: C, 39.71; H, 3.31; N, 8.06. Found: C, 38.77; H, 3.50; N, 7.82. $^1$H NMR (400 MHz, CD$_3$CN): δ 1.35 (t, 6H, CH$_3$, J=7.28), 4.28 (q, 4H, —CH$_2$—, J=3.64), 6.44 (d, 1H, J=7.01), 7.03 (t, 1H, J=7.40), 7.12 (t, 1H, J=7.55), 7.37 (m, 2H), 7.59 (m, 2H), 7.88 (d, 1H, J=8.10), 7.99 (d, 1H, J=7.96), 8.12 (t, 1H, J=8.05), 8.22 (m, 3H). $^{13}$C NMR (126 MHz, CD$_3$CN): δ 15.87 (Et), 46.59 (Et), 120.45, 120.76, 125.32, 125.93, 126.51, 129.69, 132.51, 137.97, 141.71, 142.58, 153.27 (carbene). $^{31}$P NMR (400 MHz, CD$_3$CN): δ −144.52. $^{19}$F NMR (400 MHz, CD$_3$CN): δ −72.46. FAB-MS (+ve, m/z): 550 [M$^+$].

Complex 13. Yield: 70.1 mg, 78.6%. Anal. Calcd for C$_{25}$H$_{27}$N$_4$PF$_6$Pt: C, 41.49; H, 3.73; N, 7.75. Found: C, 42.36; H, 3.95; N, 8.07. $^1$H NMR (400 MHz, CD$_3$CN): δ 0.74 (t, 6H, J=7.39, —CH$_3$ on -$^n$Pr), 1.82 (sestet, 4H, J=7.33, —CH$_2$— on -$^n$Pr), 4.24 (t, 4H, J=7.11, —N—CH$_2$— on -$^n$Pr), 6.41 (d, 1H, J=7.36), 6.95 (t, 1H, J=7.38), 7.03 (t, 1H, J=8.04), 7.50-7.52 (m, 2H), 7.61 (d, 1H, J=7.59), 7.70 (t, 1H, J=6.49), 8.00 (dd, 1H, J=5.34) 8.15-8.19 (m, 2H), 8.32 (t, 1H, J=7.88), 8.38 (d, 1H, J=5.35), 8.47 (d, 1H, J=8.03). $^{31}$P NMR (400 MHz, CD$_3$CN): δ −144.25. $^{19}$F NMR (400 MHz, CD$_3$CN): δ −73.66. FAB-MS (+ve, m/z): 578 [M$^+$].

Complex 14. Yellow crystal available for single crystal X-ray diffraction was formed by slow diffusion of Et$_2$O into CH$_3$CN. Yield: 70.1 mg, 78.6%. Anal. Calcd for C$_{27}$H$_{31}$N$_4$PF$_6$Pt: C, 43.14; H, 4.13; N, 7.46. Found: C, 42.86; H, 4.26; N, 7.51. $^1$H NMR (400 MHz, CD$_3$CN): δ 0.75 (t, 6H, J=7.36, —CH$_3$ on -$^n$Bu), 1.22 (sextet, 4H, J=7.50, —CH$_2$— on -$^n$Bu), 1.79 (sextet, 4H, J=7.53, —CH$_2$— on -$^n$Bu), 4.19-4.26 (m, 4H, —N—CH$_2$— on -$^n$Bu), 6.47 (d, 1H, J=7.43), 7.03 (t, 1H, J=6.78), 7.12 (t, 1H, J=7.52), 7.32-7.36 (m, 2H), 7.60 (d, 2H, J=6.74), 7.88 (d, 1H, J=8.09), 7.99 (d, 1H, J=7.90), 8.12 (t, 1H, J=8.06), 8.23 (m, 3H). $^{31}$P NMR (400 MHz, CD$_3$CN): δ −144.52. $^{19}$F NMR (400 MHz, CD$_3$CN): δ −73.86. FAB-MS (+ve, m/z): 606 [M$^+$].

Complex 15. Orange crystal available for single crystal X-ray diffraction was formed by slow diffusion of Et$_2$O into CH$_3$CN. Yield: 37.2 mg, 82.0%. Anal. Calcd for C$_{47}$H$_{46}$N$_8$P$_2$F$_{12}$Pt$_2$: C, 40.23; H, 3.28; N, 7.99. Found: C, 41.06; H, 3.41; N, 8.18. $^1$H NMR (400 MHz, CD$_3$CN): δ 0.58-0.64 (m, 6H, -$^n$Bu), 0.9)-1.12 (m, 4H, -$^n$Bu), 1.63-1.78 (m, 4H, -$^n$Bu), 3.93-4.19 (m, 4H, -$^n$Bu), 6.21 (d, 1H, J=7.05), 6.29 (d, 1H, J=7.56), 6.33 (d, 1H, J=7.56), 6.65 (t, 1H, J=7.42), 6.71 (t, 1H, J=7.41), 6.84-6.88 (m, 3H), 7.11-7.16 (m, 3H), 7.22 (d, 1H, J=7.42), 7.41-7.45 (m, 3H), 7.55 (d, 1H, J—7.43), 7.55-7.61 (m, 2H), 7.80-7.87 (m, 6H), 7.95-8.00 (m, 4H). $^{13}$C NMR (126 MHz, CD$_3$CN): δ 13.64 (-$^n$Bu), 19.86 (-$^n$Bu), 33.12 (-$^n$Bu), 51.40 (-$^n$Bu), 120.36, 120.59, 120.98, 122.59, 122.77, 124.07, 124.37, 125.42, 125.73, 126.71, 129.07, 129.34, 131.97, 132.18, 136.96, 141.41, 152.35 (carbene), 162.28 (carbene). $^{31}$P NMR (400 MHz, CD$_3$CN): δ −144.51. $^{19}$F NMR (400 MHz, CD$_3$CN): δ −72.87. FAB-MS (+ve, m/z): 1257 [M$^+$+PF$_6$], 1112 [M$^+$].

Complex 16. Yield: 37.2 mg, 82.0%. Anal. Calcd for C$_{49}$H$_{50}$N$_8$P$_2$F$_{12}$Pt$_2$: C, 41.12; H, 3.50; N, 7.83. Found: C, 41.06; H, 3.41; N, 8.08. $^1$H NMR (400 MHz, CD$_3$CN): δ 0.62-0.70 (m, 3H), 0.75 (t, 3H, J=7.33), 0.86 (t, 2H, J=7.33), 0.92-0.99 (m, 2H), 1.04-1.14 (m, 2H), 1.17-1.24 (m, 2H), 1.56-1.70 (m, 2H), 1.76-1.85 (m, 2H), 2.33-2.50 (m, 2H), 3.98-4.13 (m, 2H), 6.26-6.31 (m, 1H), 6.49 (t, 1H, J=7.52), 6.81 (t, 1H, J=6.89), 6.85 (t, 1H, J=7.45), 6.92 (t, 1H, J=7.65), 6.99-7.09 (m, 2H), 7.12-7.18 (m, 2H), 7.20 (t, 1H, J=8.17), 7.35-7.49 (m, 5H), 7.58-7.63 (m, 2H), 7.71 (d, 1H, J=8.07), 7.80-7.85 (m, 1H), 7.90-7.93 (m, 1H), 7.99-8.07 (m, 2H), 8.09-8.17 (m, 2H), 8.17-8.24 (m, 2H). $^{13}$C NMR (126 MHz, CD$_3$CN): δ 13.76, 20.14, 23.81, 33.12, 51.40, 51.78, 120.43, 120.73, 122.38, 122.84, 124.47, 125.27, 125.97, 126.44, 129.55, 129.96, 131.21, 132.46, 137.93, 142.77, 162.47 (carbene), 165.18 (carbene). $^{31}$P NMR (400 MHz, CD$_3$CN): δ −144.53. $^{19}$F NMR (400 MHz, CD$_3$CN): δ −72.90. FAB-MS (+ve, m/z): 1285 [M$^+$+PF$_6$], 1140 [M$^+$]

Complex 17. Yield: 75.9 mg, 94.0%. Anal. Calcd for C$_{31}$H$_{32}$N$_4$PF$_6$Pt: C, 46.50; H, 4.03; N, 7.00. Found: C, 46.86; H, 4.28; N, 7.32. $^1$H NMR (400 MHz, CD$_3$CN): δ 0.81 (t, 6H, J=6.15, —CH$_3$ on -$^n$Pr), 1.80-1.89 (m, 4H, —CH$_2$— on -$^n$Pr), 4.19-4.25 (m, 4H, —CH$_2$—N on -$^n$Pr), 6.51 (d, 1H, J=7.40), 7.05 (t, 1H, J=7.38), 7.14 (t, 1H, J=7.24), 7.34-7.38 (m, 2H), 7.58-7.66 (m, 4H), 7.74 (d, 1H, J=6.55), 7.94-7.98 (m, 2H), 8.13 (s, 1H), 8.23-8.28 (m, 3H), 8.41 (d, 1H, J=7.98). $^{13}$C NMR (126 MHz, CD$_3$CN): δ 11.28 (-$^n$Pr), 24.64 (-$^n$Pr), 53.34 (-$^n$Pr), 122.71, 125.45, 125.84, 126.63, 128.62, 130.37, 131.58, 132.49, 137.94, 141.61, 153.20, 154.82, 155.77, 165.33 (carbene). $^{31}$P NMR (400 MHz, CD$_3$CN): δ −144.54. $^{19}$F NMR (400 MHz, CD$_3$CN): δ −73.79. FAB-MS (+ve, m/z): 807 [M$^+$].

Complex 18. Yield: 54.1 mg, 90.3%. Anal. Calcd for C$_{39}$H$_{48}$N$_4$PF$_6$Pt: C, 51.31; H, 5.30; N, 6.14. Found: C, 52.63; H, 5.51; N, 6.35. $^1$H NMR (400 MHz, CD$_3$CN): δ 0.82 (t, 6H, J=7.38, -$^n$Pr), 1.44 (s, 18H, -$^t$Bu), 1.80-1.86 (m, 4H, -$^n$Pr), 4.16-4.25 (m, 4H, -$^n$Pr), 6.09 (t, 2H, J=6.31), 6.51 (d, 1H, J=7.39), 7.05 (t, 1H, J=7.41), 7.15 (t, 1H, J=7.55), 7.35-7.38 (m, 2H), 7.58-7.63 (m, 1H), 7.70-7.73 (m, 2H), 7.79 (d, 1H, J=7.69), 8.10 (s, 1H), 8.22-8.26 (m, 2H), 8.46 (d, 1H, J=7.99). $^{13}$C NMR (126 MHz, CDCl$_3$): δ 10.77 (-$^n$Pr), 24.65 (-$^n$Pr), 31.65 (-$^t$Bu), 53.38 (-$^n$Pr), 122.71, 123.11, 125.78, 126.77, 129.62, 132.43, 137.81, 149.67, 141.52, 148.89, 153.26, 155.57, 159.25, 165.16 (carbene). $^{31}$P NMR (400 MHz, CD$_3$CN): δ −144.73. $^{19}$F NMR (400 MHz, CD$_3$CN): δ −72.93. FAB-MS (+ve, m/z): 768 [M$^+$].

Complex 19. Yield: 81.9 mg, 41.4%. Anal. Calcd for C$_{59}$H$_{56}$N$_2$P$_2$F$_{12}$Pt$_2$: C, 45.51; H, 3.62; N, 7.20. Found: C, 45.82; H, 3.72; N, 7.26. $^1$H NMR (400 MHz, CD$_3$CN): δ 0.58-0.64 (m, 6H, -$^n$Bu), 0.98-1.38 (m, 8H, -$^n$Bu), 3.89-4.06 (m, 4H, -$^n$Bu), 6.20-6.49 (m, 3H), 6.67-6.75 (m, 2H), 6.89-6.93 (m, 2H), 7.12-7.16 (m, 2H), 7.31 (d, 1H, J=7.61), 7.39-7.46 (m, 6H), 7.50-7.54 (m, 2H), 7.59-7.67 (m, 4H), 7.71-7.76 (m, 4H), 7.83-7.88 (m, 4H), 7.98-8.04 (m, 4H), 8.18 and 8.31 (m, 2H). $^{13}$C NMR (126 MHz, CD$_3$CN): δ 13.63 (-$^n$Bu), 19.86 (-$^n$Bu), 33.01 (-$^n$Bu), 51.29 (-$^n$Bu), 125.67, 126.91, 128.41, 131.72, 131.98, 136.87, 141.27, 145.21, 152.29, 154.46, 155.52, 156.24, 165.45 (carbene). $^{31}$P NMR (400 MHz, CD$_3$CN): δ −144.69. $^{19}$F NMR (400 MHz, CD$_3$CN): δ −72.97. FAB-MS (+ve, m/z): 1413 [M$^+$+PF$_6$], 1268 [M$^+$].

Complex 20. Yield: 56.6 mg, 52.5%. Anal. Calcd for C$_{75}$H$_{88}$N$_8$P$_2$F$_{12}$Pt$_2$: C, 50.56; H, 4.98; N, 6.29. Found: C, 57.21; H, 5.09; N, 6.43. $^1$H NMR (400 MHz, CD$_3$CN): δ 0.79-0.83 (m, 6H, -$^n$Bu), 1.10-1.22 (m, 4H, -$^n$Bu), 1.45 (s, 36H, -$^t$Bu), 3.52-3.72 (m, 4H, -$^n$Bu), 5.93-5.96 (m, 2H), 6.24-6.30 and 6.43-6.48 (m, 2H), 6.85-6.96 (m, 2H), 7.10-7.19 (m, 2H), 7.27-7.51 (m, 4H), 7.53-7.62 (m, 4H), 7.89-

7.91 (m, 1H), 8.04-8.06 (m, 1H), 8.14-8.19 (m, 2H), 8.35-8.41 (m, 2H), 8.51 (d, 1H, J=8.81), 8.69-8.71 and 8.76-8.79 (m, 2H). $^{13}$C NMR (126 MHz, CD$_3$CN): δ 13.61 (–$^n$Bu), 19.82 (–$^n$Bu), 31.68 (–$^i$Bu), 33.03 (–$^n$Bu), 51.32 (–$^n$Bu), 126.73, 127.61, 129.41, 130.72, 131.98, 134.31, 140.69, 143.34, 151.07, 153.85, 154.97, 155.63, 165.35 (carbene). $^{31}$P NMR (400 MHz, CD$_3$CN): δ –144.75. $^{19}$F NMR (400 MHz, CD$_3$CN): δ –73.07. FAB-MS (+ve, m/z): 1637 [M$^+$+PF$_6$], 1492 [M$^+$].

Complex 21. Yield: 113.7 mg, 75.9%. Anal. Calcd for C$_{36}$H$_{39}$N$_4$PF$_6$Pt: C, 49.83; H, 4.53; N, 6.46. Found: C, 50.07; H, 4.72; N, 6.51. $^1$H NMR (400 MHz, CD$_3$CN): δ 0.79 (t, 6H, J=7.36, –$^n$Pr), 1.71-1.91 (m, 4H, –$^n$Pr), 4.31 (t, 4H, J=7.23, –$^n$Pr), 6.89 (s, 1H), 7.33-7.47 (m, 4H), 7.52-7.56 (m, 1H), 7.83-7.89 (m, 2H), 8.04 (t, 1H, J=7.58), 8.09-8.19 (m, 4H), 8.21-8.28 (m, 2H), 8.80 (d, 1H, J=6.32), 9.01-9.05 (m, 1H). $^{13}$C NMR (126 MHz, CD$_3$CN): δ 11.29 (–$^n$Pr), 24.57 (–$^n$Pr), 53.44 (–$^n$Pr), 120.51, 120.92, 122.84, 123.93, 126.25, 127.72, 128.69, 129.11, 129.77, 129.98, 131.14, 131.90, 132.35, 134.76, 135.23, 136.05, 136.57, 141.51, 147.92, 151.74, 162.56 (carbene). $^{31}$P NMR (400 MHz, CD$_3$CN): δ –145.13. $^{19}$F NMR (400 MHz, CD$_3$CN): δ –73.16. FAB-MS (+ve, m/z): 680 [M$^+$].

Complex 22. Yellow crystal available for single crystal X-ray diffraction is formed via recrystallization from CH$_3$CN/Et$_2$O. Yield: 56.6 mg, 52.5%. Anal. Calcd for C$_{66}$H$_{64}$N$_8$P$_2$F$_{12}$Pt$_2$: C, 48.06; H, 3.91; N, 6.79. Found: C, 48.32; H, 4.06; N, 6.85. $^1$H and $^{13}$C NMR: not available due to moderate solubility in common deuterated NMR solvents. FAB-MS (+ve, m/z): 1315 [M$^+$].

Complex 23. A mixture of [Pt(CNN)Cl] (45 mg, 0.098 mmol), 1-(3-hydroxy-propyl)-3-(2,4,6-trimethyl-phenyl)-imidazolium bromide (33 mg, 0.1 mmol) and KO$^t$Bu (14 mg, 0.12 mmol) were dissolved in CH$_3$CN (15 mL) and refluxed overnight. A dark yellow solution was formed. A saturated NH$_4$PF$_6$ solution in CH$_3$CN was added and stirred at 50° C. for 1 hour. The reaction mixture was treated similar to that of complex 11, orange solid was washed by Et$_2$O and dried under vacuum. Yield: 95 g (86.2%). $^1$H NMR (400 MHz, CD$_3$CN): δ=2.05 (s, 1H, —OH), 2.07 (s, 6H, —CH$_3$), 2.35 (s, 3H, —CH$_3$), 3.51-3.56 (m, 2H, -propylene-), 4.34-4.43 (m, 2H, -propylene-), 4.52-4.57 (m, 2H, -propylene-), 6.70 (d, 1H, J=7.3 Hz), 6.85 (s, 2H), 7.04-7.12 (m, 2H), 7.30 (s, 1H), 7.52 (d, 1H, J=7.5 Hz), 7.58-7.64 (m, 2H), 7.80 (d, 1H, J=8.1 Hz), 7.90 (d, 1H, J=8.0 Hz), 8.05 (t, 1H, J=8.1 Hz), 8.15-8.20 (m, 2H), 8.32 (d, 1H, J=5.3 Hz). $^{13}$C NMR (500 MHz, CD$_3$CN): δ=20.89, 34.02, 49.67, 59.36, 120.76, 123.16, 125.24, 125.45, 126.98, 126.36, 129.15, 129.67, 130.23, 132.07, 138.72, 142.53, 155.32, 165.32. FAB-MS (+ve, m/z): 671 [M$^+$]. elemental analysis calcd (%) for C$_{31}$H$_{31}$N$_4$OPF$_6$Pt: C, 45.65; H, 3.83; N, 6.87. found: C, 45.76; H, 3.85; N, 6.98.

Complex 24. A mixture of extended [Pt(CNN)Cl] (85 mg, 0.17 mmol), N,N'-di-n-propylimidazolium bromide (41 mg, 0.18 mmol) and KO$^t$Bu (21 mg, 0.19 mmol) were dissolved in CH$_3$CN (15 mL) and refluxed overnight. A clear yellow solution was formed. A saturated NH$_4$PF$_6$ solution in CH$_3$CN was added and stirred at 50° C. for 1 hour. The reaction mixture was cooled to room temperature, yellow solid was formed and collected via filtration, the solid was washed by Et$_2$O and dried under vacuum. Yield: 0.34 g (80.0%). $^1$H NMR (400 MHz, CD$_3$CN): δ=0.81 (t, 6H, J=7.4 Hz, –$^n$Pr), 1.72-1.87 (m, 4H, –$^n$Pr), 4.25 (t, 4H, J=7.2 Hz), 6.50 (d, 1H, J=7.3 Hz), 7.05 (t, 1H, J=7.0 Hz), 7.14 (t, 1H, J=7.5 Hz), 7.38-7.41 (m, 2H), 7.64 (d, 1H, J=7.0 Hz), 7.76-7.92 (m, 2H), 8.00-8.19 (m, 5H), 8.75 (s, 1H), 8.95 (s, 1H). $^{13}$C NMR (500 MHz, CD$_3$CN): δ=11.27 (–$^n$Pr), 24.61 (–$^n$Pr), 53.25 (–$^n$Pr), 120.19, 122.75, 123.89, 125.72, 126.22, 129.08, 129.99, 131.89, 132.24, 136.64, 137.78, 142.23, 156.89, 164.65. FAB-MS (+ve, m/z): 629 [M$^+$]. elemental analysis calcd (%) for C$_{29}$H$_{29}$N$_4$PF$_6$Pt: C, 45.02; H, 3.78; N, 7.24. found: C, 45.12; H, 3.97; N, 7.39.

Complex 25. A mixture of extended [Pt(CNN)Cl] (70 mg, 0.14 mmol), N-n-butyl-N'-(2-hydroxyethyl)imidazolium bromide (36 mg, 0.15 mmol) and KO$^t$Bu (19 mg, 0.16 mmol) were dissolved in CH$_3$CN (15 mL) and refluxed overnight. An clear orange solution was formed. A saturated NH$_4$PF$_6$ solution in CH$_3$CN was added and stirred at 50° C. for 1 hour. The reaction mixture was cooled to room temperature, the solvent was evaporated to give rise a yellow solid. The crude product was dissolved in CHCl$_3$. the insoluble impurities were filtered and discarded. The clear yellow filtrate was concentrated to 5 mL, excess Et$_2$O was added. The solution was stored <10° C. overnight. Yellow crystalline solid was formed and collected via filtration, the solid was washed by Et$_2$O and dried under vacuum. Yield: 95 g (86.2%). $^1$H NMR (400 MHz, CD$_3$CN): δ=0.72 (t, 3H, J=7.4 Hz, –$^n$Bu), 1.20-1.29 (m, 2H, –$^n$Bu), 1.78-1.87 (m, 2H, –$^n$Bu), 1.98 (s, 1H, —OH), 3.77-3.86 (m, 2H, –$^n$Bu), 4.25-4.32 (m, 2H, -ethylene-), 4.46-4.52 (m, 2H, -ethylene-), 6.49 (d, 1H, J=7.4 Hz), 7.05 (t, 1H, J=7.4 Hz), 7.14 (t, 1H, J=7.5 Hz), 7.39 (s, 1H), 7.45 (s, 1H), 7.63 (d, 1H, J=7.7 Hz), 7.83-7.89 (m, 2H), 8.02 (t, 1H, J=7.6 Hz), 8.09 (d, 1H, J=8.0 Hz), 8.13-8.18 (m, 3H), 8.75 (s, 1H), 9.03 (s, 1H). $^{13}$C NMR (500 MHz, CD$_3$CN): δ=13.76 (–$^n$Bu), 20.23 (–$^n$Bu), 33.18 (–$^n$Bu), 51.48 (–$^n$Bu), 54.12, 61.66, 120.12, 122.60, 123.35, 123.79, 125.72, 126.22, 129.09, 130.00, 131.88, 132.27, 135.26, 136.61, 137.73, 142.32, 148.78, 151.74, 157.38, 164.65. FAB-MS (+ve, m/z): 645 [M$^+$]. elemental analysis calcd (%) for C$_{29}$H$_{29}$N$_4$OPF$_6$Pt: C, 44.11; H, 3.70; N, 7.10. found: C, 44.36; H, 3.81; N, 7.15.

Example 2

In Vitro Cytotoxicity of the Cyclometalated N-heterocyclic Carbene Complexes

Example 2 describes the in vitro cytotoxicity, which is indicative of the induction of cell death and/or inhibition of cellular proliferation of cancer cells, of the cyclometalated N-heterocyclic complexes on cervical epithelioid carcinoma, hepatocellular carcinoma, leukemia, nasopharyngeal carcinoma, breast carcinoma, melanoma, and lung carcinoma.

By means of MTT assays, the cytotoxic properties of cyclometalated N-heterocyclic carbene complexes (1-25) were determined toward some established human cancer cell lines including hepatocellular carcinoma (HepG2), cervical epithelioid carcinoma (HeLa), epithelial carcinoma (KB and its camptothecin-resistant cell line KB 100), non-small cell lung carcinoma (NCI-H460), leukemia (HL-60), breast carcinoma (MDA-MB-231), melanoma (B16) and nasopharyngeal carcinoma (SUNE1). The IC$_{50}$ values (dose required to inhibit 50% cellular growth for 72 h) of the gold(III) complexes are listed in Table 1. All the [Au$^{III}_n$(CNC)$_n$(NHC)]$^{n+}$ complexes exhibit promising cytotoxicity toward these cell lines with IC$_{50}$ values span over the range of 0.15 to 28 μM. In terms of the IC$_{50}$ values, they display similar cytotoxic properties compared to the reference complexes cisplatin and camptothecin (CPT). Among them, complex 1 exhibits the highest cytotoxic activity toward all the cancer cell lines (except KB) and displays a ~18 to 28 fold higher cytotoxic activity than cisplatin.

Using lung fibroblast cells (CCD-19Lu), the cytotoxicity of the complexes to non-cancerous cells was also examined. As shown in Table 1, the examined complexes examined in general have higher cancer-cell specificity and results in more cytotoxic to cancer cell then the fibroblast cells.

which a, represents tumor length; b, the width; and c, tumor thickness, as measured with a caliper and expressed in milli-

TABLE 1

The IC$_{50}$ values (μM, 72 h) of [Au$^{III}$$_n$(CNC)$_n$(NHC)]$^{n+}$ complexes against selected human cancer cell lines.

| | HepG2 | HeLa | KB | KB100 | SUNE1 | NCI-H460 | MBA-MD-231 | B16 | HL-60 | CCD-19Lu |
|---|---|---|---|---|---|---|---|---|---|---|
| | | | | | IC$_{50}$ (μM) | | | | | |
| 1 | 0.37 | 0.15 | 0.56 | 1.2 | 0.25 | 0.17 | 0.62 | 00.33 | 0.48 | 25 |
| 2 | 7.9 | 7.8 | 10 | 28 | 3.3 | 3.0 | 4.2 | 10 | 5.9 | >100 |
| 3 | 1.1 | 2.4 | 2.3 | 12 | 3.0 | 1.2 | 1.7 | 2.2 | 2.6 | 16 |
| 4 | 1.9 | 2.7 | 3.6 | 4.5 | 5.5 | 6.2 | 3.7 | 7.7 | 1.1 | 11 |
| 5 | 2.6 | 3.5 | 4.4 | 4.0 | 3.4 | 9.5 | 13 | 2.1 | 1.2 | 11 |
| 6 | 18 | 3.9 | 20 | 9.4 | 0.7 | 11 | 8.5 | 3.3 | 7.1 | 48 |
| 7 | 20 | 5.6 | 15 | 6.7 | 0.9 | 12 | 8.4 | 11 | 8.2 | 20 |
| 8 | 1.0 | 0.5 | 0.42 | 18 | 0.26 | 0.18 | 0.96 | 0.56 | 0.13 | 0.89 |
| 9 | 4.5 | 7.2 | 5.0 | 3.8 | 4.5 | 5.5 | 6.2 | 9.1 | 7.1 | 9.9 |
| 10 | 2.5 | 1.1 | 1.3 | 9.5 | 4.2 | 9.6 | 3.3 | 3.4 | 7.1 | 6.5 |
| 11 | 0.31 | 0.33 | 0.66 | 0.62 | 0.51 | 0.58 | 1.5 | 3.1 | 0.58 | 5.7 |
| 12 | 1.3 | 0.48 | 0.89 | 0.77 | 0.32 | 0.57 | 1.2 | 1.8 | 0.52 | 2.1 |
| 13 | 1.1 | 0.05 | 0.14 | 0.13 | 0.16 | 0.18 | 0.28 | 0.42 | 0.56 | 12 |
| 14 | 0.77 | 0.05 | 0.04 | 0.08 | 0.14 | 0.09 | 0.04 | 0.15 | 0.08 | 10 |
| 15 | 9.4 | 8.0 | n.d. | n.d. | 6.4 | n.d. | n.d. | n.d. | n.d. | 40 |
| 16 | 7.1 | 3.9 | n.d. | n.d. | 5.6 | n.d. | n.d. | n.d. | n.d. | 27 |
| 17 | 0.49 | 0.55 | n.d. | n.d. | 0.86 | n.d. | n.d. | n.d. | n.d. | 10 |
| 18 | 0.27 | 0.62 | n.d. | n.d. | 0.22 | n.d. | n.d. | n.d. | n.d. | 4.2 |
| 19 | 0.18 | 0.25 | n.d. | n.d. | 0.53 | n.d. | n.d. | n.d. | n.d. | 6.1 |
| 20 | 0.11 | 0.46 | n.d. | n.d. | 0.37 | n.d. | n.d. | n.d. | n.d. | 1.2 |
| 21 | 0.34 | 0.89 | n.d. | n.d. | 1.2 | n.d. | n.d. | n.d. | n.d. | 3.5 |
| 22 | 1.25 | 2.5 | n.d. | n.d. | 1.2 | n.d. | n.d. | n.d. | n.d. | 6.8 |
| 23 | 0.78 | 0.48 | n.d. | n.d. | 0.94 | n.d. | n.d. | n.d. | n.d. | 7.5 |
| 24 | 0.88 | 0.55 | n.d. | n.d. | 0.71 | n.d. | n.d. | n.d. | n.d. | 12 |
| 25 | 0.68 | 0.45 | n.d. | n.d. | 0.88 | n.d. | n.d. | n.d. | n.d. | 11 |
| cisplatin | 14.6 | 14.9 | n.d. | n.d. | 2.4 | n.d. | n.d. | n.d. | n.d. | >100 | n.d. = not determined

Example 3

In Vivo Anti-cancer Property of the Cyclometalated N-heterocyclic Carbene Complexes Example 3 describes the results of in vivo cytotoxicity study of complex 1 and complex 14.

Figure 3:
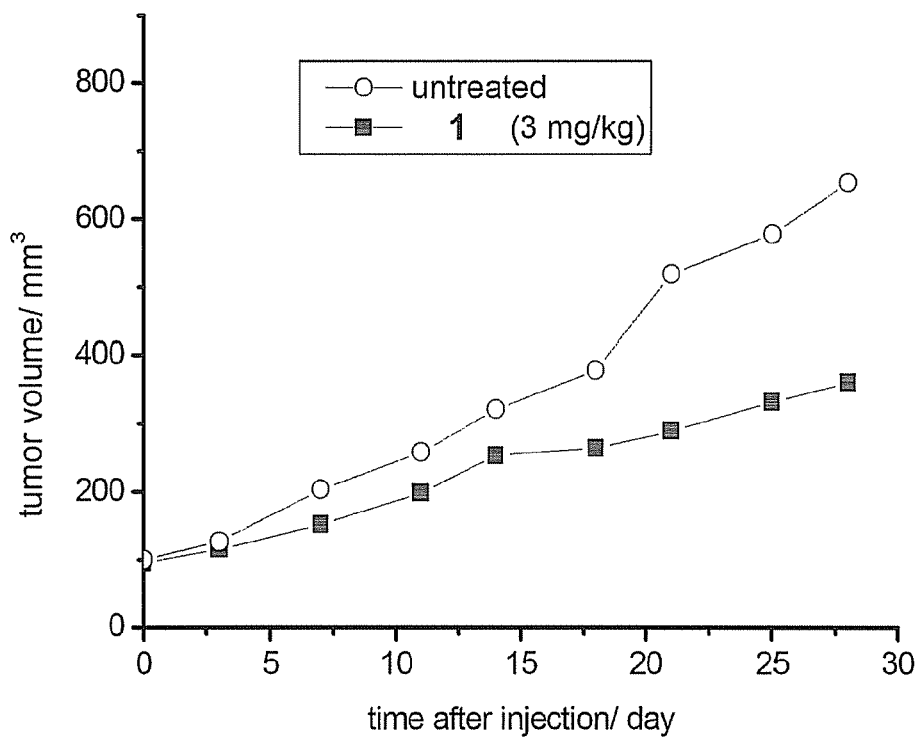
FIG. 3 shows the in vivo anti-cancer properties of complex 1 and complex 14.
Figure 3:
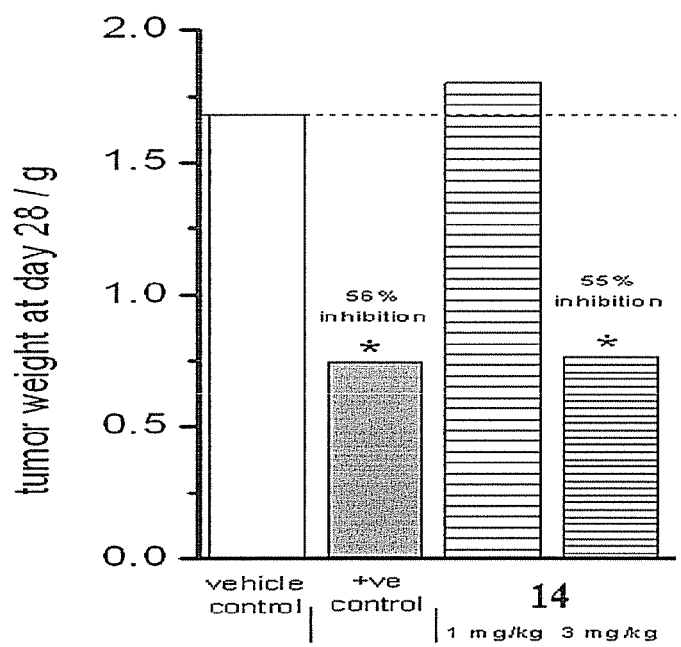

Prompted by the prominent in vitro cytotoxicity and the potential cancer-cell selectivity, the in vivo anti-cancer property of complex 1 was preliminarily examined by using nude mice models with the approval from the Committee on the Use of Live Animals for Teaching and Research (The University of Hong Kong). As shown in FIG. 3, treatment of nude mice bearing PLC tumor (hepatocellular carcinoma) by complex 1 at 3 mg/kg/week for 28 days significantly suppressed (47%) tumor growth compared to that of the vehicle control. Importantly, no apparent 1-induced toxic side-effect including death and weight loss was observed during the whole course of the examination.

For the complex 14, four-week-old male BALB/c AnN-nu mice (nude mice) were obtained from the laboratory of PearL Materia Medica Development (Shenzhen) Ltd. Tumor cells (1×10$^6$) resuspended in DMEM medium were implanted by subcutaneous injection on the right flank of the mice. When tumors were approximately 50 mm$^3$ in size, animals were randomly separated into four groups to receive treatment of twice-a-week intraperitoneal injection of 20% PET vehicle control (20% PET=12% polyethylene glycol 400; 6% ethanol; 2% Tween 20; 80% phosphate-buffered saline), complex 14 at 1 mg/kg, complex 14 at 3 mg/kg or cyclophosphamide at 30 mg/kg. Volumes of the tumor were measured every 3 to 4 days. Tumor volume was calculated by the formula: abc/2 in meter. After 28 days, the mice were sacrificed and the tumors were taken out and their weights were measured.

Results demonstrated that injection of 3 mg/kg of complex 14 significantly inhibited the NCI-H460 tumor growth by 55%, whereas 1 mg/kg was significantly less effective (FIG. 3). Regular body-weight measurement showed that mice receiving either 3 or 1 mg/kg of complex 14 had no significant weight loss.

Example 4

Induction of Apoptosis by the Cyclometalated N-heterocyclic Carbene Complexes Example 4 describes the result of studies showing that complex 1 and complex 14 would induce apoptosis in SUNE1 cancer cells.

Since cancer is characterized by uncontrolled cellular proliferation, there is a considerable interest in chemotherapeutic-induced apoptosis [J. C. Reed, Nature Rev. Drug Discov. 2002, 1, 111; D. W. Nicholson, Nature 2000, 407, 810]. Using fluorescein-labeled annexin V (AV-FITC) and propidium iodide (PI), the apoptosis-inducing properties of complex 1 in SUNE1 cells were examined by flow cytometry. Upon treatment with complex 1 (60 μM) for 72 h, 30.9% of SUNE1 cells were found to be in early apoptotic state. The apoptosis-inducing properties of complex 1 at a lower dose (12 μM for 72 h) were also examined. We found that ~90% of viable cells were unstained by both the AV-FITC and PI. The percentage of cell death in cells treated with 1 at 12 μM (IC$_{50}$ value) did not kill 50% of cells. According to the propagation profiles (formazan absorbance A$_{550nm}$ vs incubation time) of the treated SUNE1 cells, there is a trend of cellular growth inhibition in the presence of complex 1 at 12 μM level. Taken together with the flow cytometric results, complex 1 appears to inhibit cancer cell proliferation at 12 μM and induce apoptosis at higher doses (i.e. 60 μM).

The apoptosis-inducing properties of complex 14 in SUNE1 cells were also examined by flow cytometry. Upon treatment with complex 14 (10 μM) for 72 h, 46.4% of SUNE1 cells were found to be in early apoptotic state. The apoptosis-inducing properties of complex 14 at a lower dose (1 μM for 72 h) were also examined. We found that ~90% of viable cells were unstained by both the AV-FITC and PI. Thus, complex 14 could induce apoptosis at 10 μM.

Example 5

Inhibition or Poisoning of Topoisomerase by the Gold(III) Complexes

Example 5 describes the study of the topoisomerase poisoning and inhibition by complex I.

Figure 4:
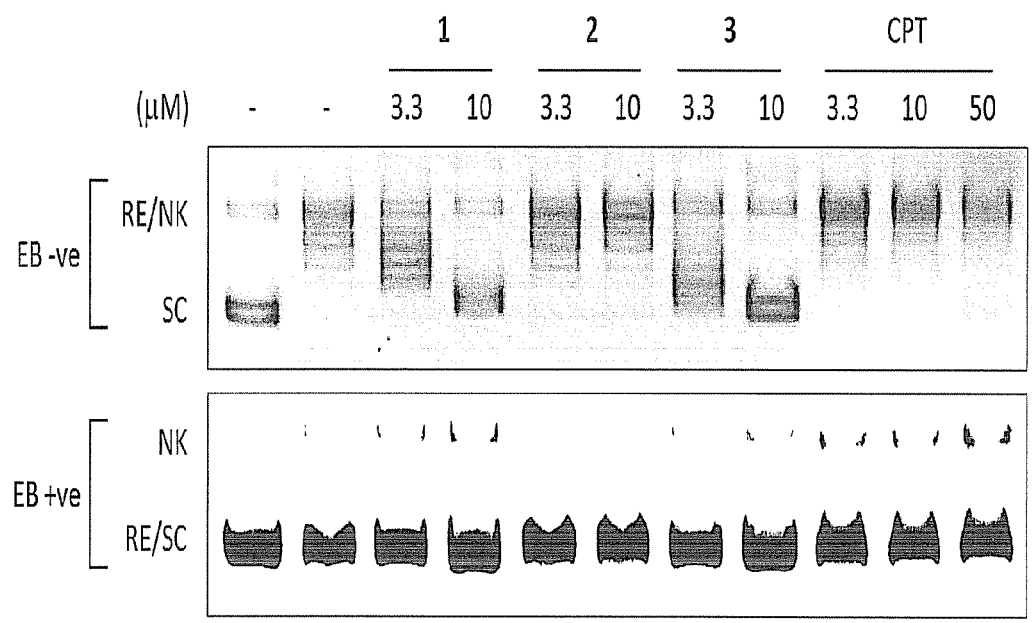
FIG. 4 shows the topoisomerase I-mediated relaxation of supercoiled DNA by complexes 1, 2, 3 and CPT.

DNA strand breaks were also detected in complex 1-treated KB cells by alkaline comet assay. The comet assay revealed that treatment with complex 1 (0.5 μM), CPT (1 μM) and a known DNA damaging agent doxorubicin (1 μg/ml) for 3 h induced extensive strand breaks on chromosomal DNA (FIG. 4). DNA cleavage events induced by CPT and complex 1, but not Dox, were partially reversed upon a second incubation at 55° C. for 10 min, suggesting that complex 1 and CPT could stabilize topoisomerase-cleavable complexes in cells. Topoisomerases have become one of the important cellular targets for anti-cancer treatment. It is believed that topoisomerase inhibitors prevent the ligation step of the cell cycle, generate DNA strand breaks, and subsequently induce apoptosis in cells. We recently have demonstrated that several platinum-based lipophilic cations and DNA intercalators such as [Pt$^{II}$(C^N^N)]$^+$ which exhibit prominent inhibitory activity on topoisomerase I. To study the impact of complex 1 on the catalytic activity of TopoI, the TopoI-mediated relaxation of supercoiled DNA was measured. Complex 1 dose-dependently inhibits DNA relaxation at significant lower concentrations than CPT (FIG. 4, upper). Higher concentration (10 μM) completely inhibited the process. The assay was repeated on ethidium bromide containing gel (FIG. 4, lower). Under the same experimental condition, the presence of nicked DNA was observed, indicating that complex 1 may stimulate DNA cleavage by TopoI.

The band depletion assay has been used to demonstrate the formation of TopoI cleavable complexes. In this assay, while TopoI-DNA cleavable complexes are trapped by alkaline lysis, free TopoI is detected as an immunoreactive band. In KB cells, both complex 1 (10 and 100 nM) and CPT (1 μM) reduced the band intensity of the TopoI band with about equal efficiency.

Figure 5:
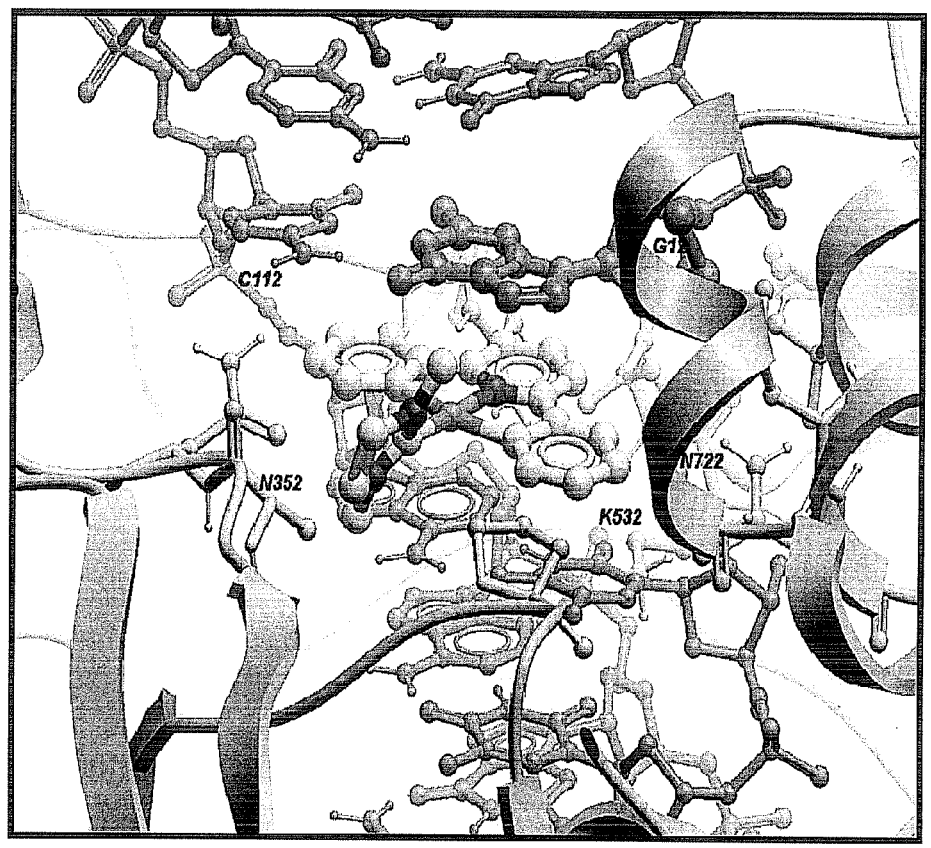
FIG. 5 shows the molecular modeling of complex 1 interacting with topoisomerase I-DNA. The topoisomerase I is in the ribbon representation and colored in yellow, while DNA is colored in green and is in a ball and stick model of complex 1.

To gain further insight into the structural basis of the TopoI-linked DNA complex stabilization by complex 1, we used flexible-ligand docking module of ICM-Pro 3.6-1 molecular software (Molsoft). Analysis of the low energy metal complex conformations suggested that complex 1 binds to TopoI-linked DNA in a similar manner to topotecan (FIG. 5), with a strong binding interaction (as reflected by the score of −34.57). The top-scoring binding pose of 1 is characterized by the C^N^C motif being in close contact with amino acid residue G12, C112, K532, N722 and the carbene group of complex 1 pointing towards N352.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A pharmaceutical composition for treatment of cancer comprising a cyclometalated N-heterocyclic carbene complex having the formula I:

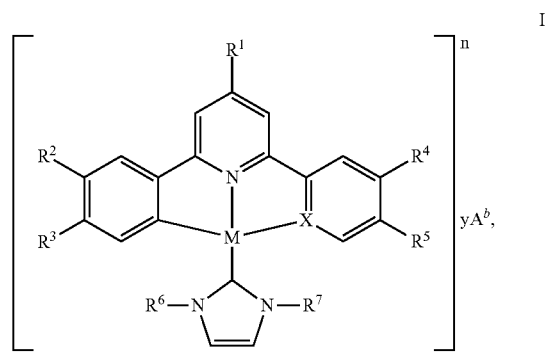

or a pharmaceutically acceptable salt thereof, wherein, either:
M is Au$^{3+}$;
X is a carbon atom;
R$^1$, R$^2$, R$^3$, R$^4$, and R$^5$ are each —H;
R$^6$ is

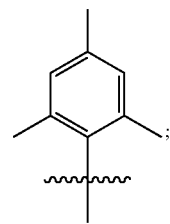

R$^7$ is

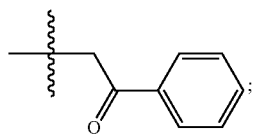

A is a OSO$_2$CF$_3$ anion;
n is +1;
b is −1; and
y is 1; or

M is Au³⁺;
X is a carbon atom;
R¹ is

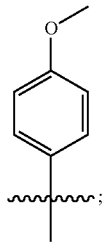 [SMILES: *c1ccc(OC)cc1]

each pair of R² and R³, and R⁴ and R⁵ is joined together to form

R⁶ and R⁷ are each —CH₃;
A is a OSO₂CF₃ anion;
n is +1;
b is −1; and
y is 1.

2. The pharmaceutical composition of I of claim 1, wherein,
M is Au³⁺;
X is a carbon atom;
R¹, R², R³, R⁴, and R⁵ are each —H;
R⁶ is

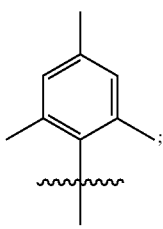

R⁷ is

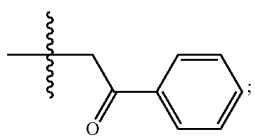 [SMILES: *CC(=O)c1ccccc1]

A is a OSO₂CF₃ anion;
n is +1;
b is −1; and
y is 1.

3. The pharmaceutical composition of I of claim 1, wherein,
M is Au³⁺;
X is a carbon atom;
R¹ is

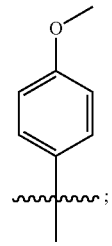

each pair of R² and R³, and R⁴ and R⁵ is joined together to form

R⁶ and R⁷ are each —CH₃;
A is a OSO₂CF₃ anion;
n is +1;
b is −1; and
y is 1.

4. A method of making the cyclometalated N-heterocyclic carbene complex of claim 1, comprising:
reacting a cyclometalated complex with a N-heterocyclic carbene compound to form the cyclometalated N-heterocyclic carbene complex of claim 1.

5. The method of claim 4 wherein the cyclometalated complex comprises a gold atom coordinated to a di-anionic substituted or non-substituted 2,6-diphenylpyridine ligand.

6. A pharmaceutical composition for treatment of cancer comprising a cyclometalated N-heterocyclic carbene complex having the formula I:

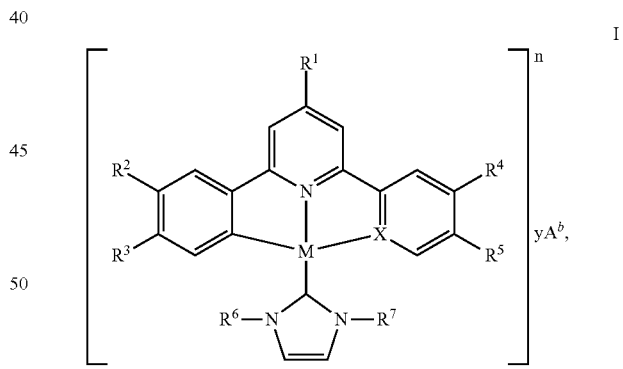

or a pharmaceutically acceptable salt thereof, wherein, either:
M is Pt²⁺;
X is a nitrogen atom;
R¹, R², R³, R⁴, and R⁵ are each —H;
R⁶ and R⁷ are each —CH₃;
A is a PF⁶ anion;
n is +1;
b is −1; and
y is 1; or
M is Pt²⁺;
X is a nitrogen atom;
R¹, R², R³, R⁴, R⁵ are each —H;
R⁶ and R⁷ are each —C₂H₅;

A is a PF⁶ anion;
n is +1;
b is −1; and
y is 1; or
M is Pt²⁺;
X is a nitrogen atom;
R¹, R², R³, R⁴, and R⁵ are each —H;
R⁶ and R⁷ are each —C₃H₇;
A is a PF⁶ anion;
n is +1;
b is −1; and
y is 1; or
M is Pt²⁺;
X is a nitrogen atom;
R¹, R², R³, R⁴, and R⁵ are each —H;
R⁶ and R⁷ are each —C₄H₉;
A is a PF⁶ anion;
n is +1;
b is −1; and
y is 1; or
M is Pt²⁺;
X is a nitrogen atom;
R¹ is

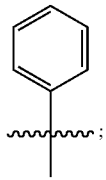 [SMILES: *c1ccccc1]

R², R³, R⁴, and R⁵ are each —H;
R⁶ and R⁷ are each —C₃H₇;
A is a PF⁶ anion;
n is +1;
b is −1; and
y is 1; or
M is Pt²⁺;
X is a nitrogen atom;
R¹ is

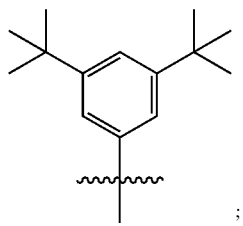 [SMILES: *c1cc(C(C)(C)C)cc(C(C)(C)C)c1]

R², R³, R⁴, and R⁵ are each —H;
R⁶ and R⁷ are each —C₃H₇;
A is a PF⁶ anion;
n is +1;
b is −1; and
y is 1.

7. The pharmaceutical composition of I of claim 6, wherein,
M is Pt²⁺;
X is a nitrogen atom;
R¹, R², R³, R⁴, and R⁵ are each —H;
R⁶ and R⁷ are each —CH₃;
A is a PF⁶ anion;
n is +1;
b is −1; and
y is 1.

8. The pharmaceutical composition of I of claim 6, wherein,
M is Pt²⁺;
X is a nitrogen atom;
R¹, R², R³, R⁴, and R⁵ are each —H;
R⁶ and R⁷ are each —C₂H₅;
A is a PF⁶ anion;
n is +1;
b is −1; and
y is 1.

9. The pharmaceutical composition of I of claim 6, wherein,
M is Pt²⁺;
X is a nitrogen atom;
R¹, R², R³, R⁴, and R⁵ are each —H;
R⁶ and R⁷ are each —C₃H₇;
A is a PF⁶ anion;
n is +1;
b is −1; and
y is 1.

10. The pharmaceutical composition of I of claim 6, wherein,
M is Pt²⁺;
X is a nitrogen atom;
R¹, R², R³, R⁴, and R⁵ are each —H;
R⁶ and R⁷ are each —C₄H₉;
A is a PF⁶ anion;
n is +1;
b is −1; and
y is 1.

11. The pharmaceutical composition of I of claim 6, wherein,
M is Pt²⁺;
X is a nitrogen atom;
R¹ is

R², R³, R⁴, and R⁵ are each —H;
R⁶ and R⁷ are each —C₃H₇;
A is a PF⁶ anion;
n is +1;
b is −1; and
y is 1.

12. The pharmaceutical composition of I of claim 6, wherein,
M is Pt²⁺;
X is a nitrogen atom;

$R^1$ is

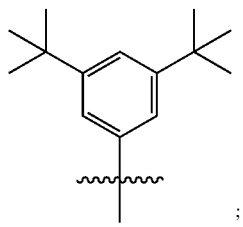 [SMILES: *c1cc(C(C)(C)C)cc(C(C)(C)C)c1]

$R^2$, $R^3$, $R^4$, and $R^5$ are each —H;
$R^6$ and $R^7$ are each —$C_3H_7$;
A is a $PF^6$ anion;
n is +1;
b is −1; and
y is 1.

13. A method of making the cyclometalated N-heterocyclic carbene complex of claim 6, comprising:
    reacting a cyclometalated complex with a N-heterocyclic carbene compound to form the cyclometalated N-heterocyclic carbene complex of claim 6.

14. The method of claim 13 wherein the cyclometalated complex comprises a platinum atom coordinated to a monoanionic substituted or non-substituted 6-phenyl-2,2'-bipyridine ligand.

15. A pharmaceutical composition for treatment of cancer comprising a cyclometalated N-heterocyclic carbene complex having the formula I:

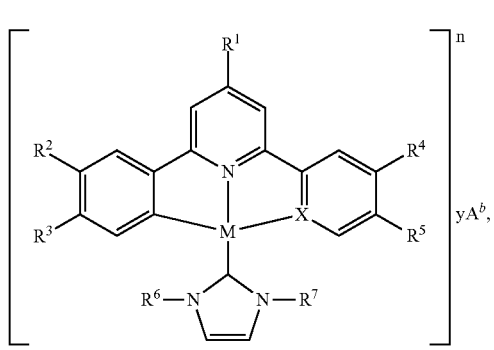

or a pharmaceutically acceptable salt thereof, wherein, either:
M is $Pt^{2+}$;
X is a nitrogen atom;
$R^1$ is —H;
each pair of $R^2$ and $R^3$, and $R^4$ and $R^5$ is joined together to form

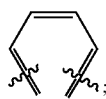 [SMILES: *=C/C=C\C=*]

$R^6$ and $R^7$ are each —$C_3H_7$;
A is a $PF_6$ anion;
n is +1;
b is −1; and
y is 1; or
M is $Pt^{2+}$;

X is a nitrogen atom;
$R^1$, $R^2$, $R^3$, $R^4$, and $R^5$ are each —H;
$R^6$ is

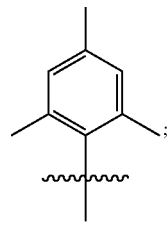

$R^7$ is —$C_3H_6OH$;
A is a $PF^6$ anion;
n is +1;
b is −1; and
y is 1; or
M is $Pt^{2+}$;
X is a nitrogen atom;
$R^1$, $R^2$ and $R^3$ are each —H;
$R^4$ and $R^5$ are joined together to form

$R^6$ and $R^7$ are each $C_3H_7$;
A is a $PF^6$ anion;
n is +1;
b is −1; and
y is 1; or
M is $Pt^{2+}$;
X is a nitrogen atom;
$R^1$, $R^2$ and $R^3$ are each —H;
$R^4$ and $R^5$ are joined together to form

$R^6$ is $C_4H_9$;
$R^7$ is —$C_2H_4OH$;
A is a $PF^6$ anion;
n is +1;
b is −1; and
y is 1.

16. The pharmaceutical composition of I of claim 15, wherein,
M is $Pt^{2+}$;
X is a nitrogen atom;
$R^1$ is —H;
each pair of $R^2$ and $R^3$, and $R^4$ and $R^5$ is joined together to form

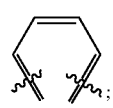

$R^6$ and $R^7$ are each —$C_3H_7$;
A is a $PF_6$ anion;
n is +1;
b is −1; and
y is 1.

17. The pharmaceutical composition of I of claim 15, wherein,
M is $Pt^{2+}$;
X is a nitrogen atom;
$R^1$, $R^2$, $R^3$, $R^4$, and $R^5$ are each —H;
$R^6$ is

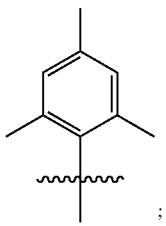

$R^7$ is —$C_3H_6OH$;
A is a $PF^6$ anion;
n is +1;
b is −1; and
y is 1.

18. The pharmaceutical composition of I of claim 15, wherein,
M is $Pt^{2+}$;
X is a nitrogen atom;
$R^1$, $R^2$ and $R^3$ are each —H;
$R^4$ and $R^5$ are joined together to form

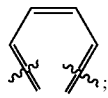

$R^6$ and $R^7$ are each $C_3H_7$;
A is a $PF^6$ anion;
n is +1;
b is −1; and
y is 1.

19. The pharmaceutical composition of I of claim 15, wherein,
M is $Pt^{2+}$;
X is a nitrogen atom;
$R^1$, $R^2$ and $R^3$ are each —H;
$R^4$ and $R^5$ are joined together to form

$R^6$ is $C_4H_9$;
$R^7$ is —$C_2H_4OH$;
A is a $PF^6$ anion;
n is +1;
b is −1; and
y is 1.

20. A method of making the cyclometalated N-heterocyclic carbene complex of claim 15, comprising:
reacting a cyclometalated complex with a N-heterocyclic carbene compound to form the cyclometalated N-heterocyclic carbene complex of claim 15.

21. The method of claim 20 wherein the cyclometalated complex comprises a platinum atom coordinated to a monoanionic substituted or non-substituted 6-phenyl-2,2'-bipyridine ligand.

* * * * *